United States Patent [19]
Snow et al.

[11] Patent Number: 5,532,150
[45] Date of Patent: Jul. 2, 1996

[54] LOW DIOL POLYALKYLENE OXIDE BIOLOGICALLY ACTIVE PROTEINACEOUS SUBSTANCES

[75] Inventors: Robert A. Snow, West Chester; David L. Ladd, Wayne; Denton W. Hoyer, Exton, all of Pa.

[73] Assignee: Sterling Winthrop, Inc., New York, N.Y.

[21] Appl. No.: 245,999

[22] Filed: May 19, 1994

Related U.S. Application Data

[63] Continuation-in-part of Ser. No. 936,416, Aug. 27, 1992, abandoned.

[51] Int. Cl.$^6$ ..................................................... C12N 9/96
[52] U.S. Cl. ............................................................ 435/188
[58] Field of Search ...................................... 435/181, 188

[56] References Cited

U.S. PATENT DOCUMENTS 4,179,337  12/1979  Davis et al. ............................ 435/181

FOREIGN PATENT DOCUMENTS 0200467  1/1979  European Pat. Off. .

OTHER PUBLICATIONS

Abuchowski, A. et al, Cancer Biochem. Biophysics, 1984, vol. 7, pp. 175–186.
Abuchowski, A., Doctor of Philosophy Thesis, "Effects of Covalent Attachment of Polyethylene Glycol on Bovine Serum Albumin and Bovine Liver Catalase", Rutgers University, New Brunswick, NJ, USA, Oct. 1975.
Veronese, F. M. et al, J. of Pharm & Pharmacol., 35, pp. 757–758 (1983).
Veronese, F. M. et al, J. of Controlled Release, 10, pp. 145–154 (1989).
Zalipsky, S. et al, Eur. Polym. J., 12, pp. 1177–1183 (1983).
Kazo, G. M., Master of Science in Biochemistry Thesis, "Modification of Proteins with Activated Polyethylene Glycols", Rutgers University, New Brunswick, NJ, Oct. 1985.

*Primary Examiner*—John W. Rollins
*Attorney, Agent, or Firm*—William J. Davis; Paul E. Dupont; Imre Balogh

[57] ABSTRACT

Disclosed are pharmaceutical compositions containing low diol polyethylene glycol, covalently attached to superoxide and dismutase process of making the compositions. Also disclosed is a method of treatment of disease processes associated with the adverse effects on tissue of superoxide anions, such as ischemic events, reperfusion injury, trauma and inflammation.

8 Claims, 22 Drawing Sheets

LOW DIOL POLYALKYLENE OXIDE BIOLOGICALLY ACTIVE PROTEINACEOUS SUBSTANCES

This is a continuation-in-part of application Ser. No. 07/936,416, filed on Aug. 27, 1992, now abandoned.

BACKGROUND OF THE INVENTION

1. Field of the Invention

This invention relates to improved composition of matter containing polyalkylene oxide and a biologically active proteinaceous substance, process of making the composition of matter and method of using the same for the treatment of disease processes associated with various physiological disorders in which the administration of the biologically active proteinaceous substance effects an immune response.

More particularly, this invention relates to improved composition of matter containing polyethylene glycol-superoxide dismutase, process of making the composition of matter and method of using the same for the treatment of disease processes associated with the adverse effects on tissue of superoxide anions, such as ischemic events, reperfusion injury, trauma and inflammation.

2. Reported Developments

Biologically active proteins, particularly enzymes and peptide hormones, have been long considered as ideal drugs for the treatment of various diseases due to their specificity and rapid catalytic action. Such enzymes include:

Oxidoreductases such as: Urate: oxygen oxidoreductase (1.7.3.3; "uricase"); Hydrogen-peroxide: hydrogen-peroxide oxidoreductase (1.11.1.6; "catalase"); Cholesterol, reduced—NADP: oxygen oxidoreductase (20-β-hydroxylating) (1.14.1.9; "Cholesterol 20-hydroxylase").

Transferases such as: UDP glucuronate glucuronyl-transferase (acceptor unspecific) (2.4.1.17; "UDP glucuronyltransferase"); UDP glucose: α-D-Galactose-1-phosphate uridylyltransferase 2.7.7.12).

Hydrolases such as: Mucopeptide N-acetylmuramyl-hydrolase (3.2.1.17; lysozyme); Trypsin (3.4.4.4); L-Asparagine aminohydrolase (3.5.1.1; "Asparaginase").

Lyases such as: Fructose-1,6-diphosphate D-glyceraldehyde-3-phosphate-lyase (4.1.2.12; "aldolase").

Isomerases such as D-Xylose ketol-isomerase (5.3.1.5; xylose isomerase) and

Ligases such as: L-Citrulline: L-aspartate ligase (AMP) (6.3.4.5).

The peptide hormones include:

Insulin, ACTH, Glucagon, Somatostatin, Somatotropin, Thymosin, Parathyroid hormone, Pigmentary hormones, Somatomedin, Erythropoietin, Luteinizing hormone, Chorionic Gonadotropin, Hypothalmic releasing factors, Antidiuretic hormones, Thyroid stimulating hormone, Calcitonin and Prolactin.

However, with minor exceptions, enzyme therapy, particularly with non-human enzymes, has been less than successful due in part to the enzymes' relatively short half-lives and to their respective immunogenicities. Upon administration, the host defense system responds to remove the foreign enzymes by initiating the production of antibodies thereto, thereby substantially reducing or eliminating their therapeutic efficacies. Repeated administration of foreign and of otherwise short lived human enzymes is essentially ineffective, and can be dangerous because of concomitant allergic response. Various attempts have been taken to solve these problems, such as through microencapsulation, entrapment in liposomes, genetic engineering and attachment of the enzymes to polymers. Among the attempts the most promising appears to be the chemical attachment of the proteinaceous substances to polyalkylene oxide (PAO) polymers and particularly polyethylene glycols (PEG). The following illustrates these attempts.

U.S. Pat. No. 4,179,337 discloses the use of polyethylene glycol or polypropylene glycol coupled to proteins to provide a physiologically active non-immunogenic water soluble polypeptide composition in which the polyethylene glycol (hereinafter sometimes referred to as PEG) serves to protect the polypeptide from loss of activity without inducing substantial immunogenic response. The methods described in the patent for the coupling of polyethylene glycol to a protein involve either the conversion of a protein amino group into an amide or pseudoamide, with consequent loss of charge carrying capacity of the amino group, or the introduction at the amino group of the protein, or vicinal to it, of a heteroatom substituent such as a hydroxyl group or of a ring system that is not repeated in the polymer backbone.

Veronese, F. M., Boccu, E., Schaivon, O., Velo, G. P., Conforti, A., Franco, L., and Milanino, R., in *Journal of Pharmacy and Pharmacology*, 35, 757–758 (1983), reported that when bovine erythrocyte derived superoxide dismutase is modified with a polyethylene glycol carboxylic acid N-hydroxysuccinimide active ester, the half-life of the enzyme in rats is increased over that of the unmodified protein.

European Patent Application 0 200 467 of Anjinomoto, Inc. describes superoxide dismutase that is chemically modified by a polyalkylene oxide (PAO) which is functionalized at both ends of the polymer with activated carboxyl coupling groups, each capable of reacting with protein. Because the activated coupling sites are located at opposite ends of the polymer chain, it is unlikely that the presence of an activated group at one end of the polymer can have a significant effect on the reactive nature of the group at the other end of the polymer. These polymers are capable of reacting at both ends to cross-couple with proteins to form copolymers between the protein and the polyalkylene oxide. Such copolymers do not have well defined or molecularly stoichiometric compositions.

Veronese, F. M. et al in *Journal of Controlled Release*, 10, 145–154 (1989) report that the derivatization with monomethoxypolyethylene glycol (hereinafter sometimes referred to as MPEG) of superoxide dismutase (hereinafter sometimes referred to as SOD) gives a heterogenous mixture of products. Heterogeneity was demonstrated to depend on the presence of bifunctional polyethylene glycol (DPEG) in the monofunctional methoxylated molecules.

These attempts, in general, have resulted in longer half-life and reduced immunogenicity of the proteinaceous biologically active substances. However, further improvements are needed in order to successfully treat a variety of diseases with these promising biologicals.

We have now discovered that biologically active proteinaceous substances can be made to possess longer half-life and less immunogenic properties by chemically modifying them using low diol polyalkylene oxide, particularly low diol polyethylene glycol (hereinafter sometimes referred to as LDPEG).

The invention will be described with specific reference to SOD, however, it is to be understood that other biologically active substances may also be chemically modified using low diol polyalkylene oxides (hereinafter sometimes referred to as LDPAO).

SUMMARY OF THE INVENTION

In accordance with the present invention, the half-life of biologically active proteins is increased and their immunogenicity is reduced or eliminated by covalent modification of the protein with low diol polyalkylene oxide, preferably low diol polyethylene glycol, employing a polyethylene glycol active ester intermediate.

Polyethylene glycol exists as a mixture of two forms:

One form contains one —OH group:

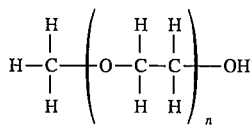

This form is called methoxylated, or more specifically, monomethoxylated polyethylene glycol since it contains one methoxy group per one molecule of polyethylene glycol.

The other form contains two OH groups.

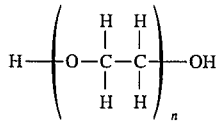

This form is called the "diol" form of polyethylene glycol since it contains two —OH groups per one molecule of polyethylene glycol.

The chain-length of the polyethylene glycol depends on the magnitude of n: the larger the n, the higher the molecular weight.

We have found that polyethylene glycol polymers having average molecular weights of from about 1,000 to about 15,000 daltons and containing not more than about 10% w/w of non-monomethoxylated polyethylene glycol are especially suitable for covalent attachment to biologically active proteins, especially to superoxide dismutase. More preferably, polyethylene glycols having average molecular weights of from about 2,000 to about 10,000 daltons and most preferably of from about 4,000 to about 6,000 daltons are used in the present invention wherein the polyethylene glycol preferably contains less than about 7% w/w and most preferably less than about 5% w/w non-monomethoxylated polyethylene glycol.

In the process of the present invention, low diol polyethylene glycol is covalently attached to the biologically active protein as shown schematically:

a) LDPEG+carboxylating agent→LDPEG-COOH b) LDPEG-COOH+carboxyl group activating agent→ active ester of LDPEG-COOH c) n (active esters of LDPEG-COOH)+Protein→(LDPEG-CO)$_n$–Protein wherein:

LDPEG-COOH is LDPEG carboxylated at hydroxyl sites; and n is the number of sites of attachment of LDPEG to protein.

LDPEG is carboxylated at the hydroxyl sites, then the carboxyl groups are esterified with a carboxyl activating agent to form the active esters which are then coupled to the protein molecule. The number of LDPEG molecules attached to the protein will vary according to the number of reactive groups, such as amino groups, present on the protein molecule.

The process of the present invention is applicable to a broad range of biologically active proteins as well as some peptide hormones. The biologically active proteins include:

Recombinant human interleukin-4 (rhuIL-4);

Protease Subtilisin Carlsberg;

Superoxide dismutases such as bovine, human, and various recombinant superoxide dismutases such as recombinant human superoxide dismutase (rhuSOD);

Oxidoreductases such as: Urate: oxygen oxidoreductase (1.7.3.3; "uricase"); Hydrogen-peroxide: hydrogen-peroxide oxidoreductase (1.11.1.6; "catalase"); Cholesterol, reduced—NADP: oxygen oxidoreductase (20-β-hydroxylating) (1.14.1.9; "Cholesterol 20-hydroxylase");

Transferases such as: UDP glucuronate glucuronyl-transferase (acceptor unspecific) (2.4.1.17; "UDP glucuronyltransferase"); UDP glucose: α-D-Galactose-1-phosphate uridylyltransferase 2.7.7.12);

Hydrolases such as: Mucopeptide N-acetylmuramyl-hydrolase (3.2.1.17; lysozyme); Trypsin (3.4.4.4); L-Asparagine aminohydrolase (3.5.1.1; "Asparaginase");

Lyases such as: Fructose-1,6-diphosphate D-glyceraldehyde-3-phosphate-lyase (4.1.2.12; "aldolase");

Isomerases such as D-Xylose ketol-isomerase (5.3.1.5; xylose isomerase) and

Ligases such as: L-Citrulline: L-aspartate ligase (AMP) (6.3.4.5).

The peptide hormones include:

Insulin, ACTH, Glucagon, Somatostatin, Somatotropin, Thymosin, Parathyroid hormone, Pigmentary hormones, Somatomedin, Erythropoietin, Luteinizing hormone, Chorionic Gonadotropin, Hypothalmic releasing factors, Antidiuretic hormones, Thyroid stimulating hormone, Calcitonin and Prolactin.

A preferred embodiment of the present invention comprises the enzyme superoxide dismutase covalently attached to low diol PEG. As used herein, the term "low diol" with respect to a polyalkylene oxide such as polyethylene glycol refers to a linear polyalkylene oxide containing not more than about 10% of non-monoalkoxylated polyalkylene oxide, and preferably not more than about 10% non-monomethoxylated polyethylene glycol. Stated another way, with respect to polyethylene oxide the term "low diol" means that more than 90% of the polyethylene glycol is monomethoxylated.

Superoxide dismutase is an intracellular enzyme present in all oxygen-metabolizing cells and is responsible for catalyzing the conversion of the superoxide radical to oxygen and hydrogen peroxide. The superoxide radical and species derived from it are believed to be causative agents in a wide variety of inflammatory disorders. Superoxide dismutase is being used to treat certain inflammatory conditions under the tradename of Orgotein. In addition, the use of SOD has been investigated for bronchopulmonary dysplasia and hyperbaric oxygen toxicity, acute inflammation caused by burns and infections, reperfusion injury following organ transplants, retrolental fibroplasia, side effects of therapeutic ionization radiation and certain dermatological conditions. However, when SOD is administered by intravenous injection to a mammal, the enzyme's half-life is only a few minutes and it disappears from circulation. As a result, the enzymatic activity is not sufficient to remove toxic substances from the bloodstream. Repeated administration on the other hand causes adverse reactions.

Low diol polyalkylene oxide (LDPAO) comprising chains of polyalkylene oxide of varying molecular weight and containing at least one hydroxyl group per chain, such as low diol polyethylene glycol (LDPEG) is attached to superoxide dismutase (SOD) to form a biologically active composition having longer half-life and less immunogenicity than either native SOD or a PAO-SOD composition.

The process of attaching LDPEG to SOD (sometimes hereinafter referred to as LDPEGation) comprises the steps of: activating low diol methoxy-PEG, having an average molecular weight of from about 1,000 to about 15,000, more preferably from 2,000 to 10,000, and most preferably from about 4,000 to 6,000 daltons, containing not more than about 10% non-monomethoxylated PEG, by succinylation to form LDPEG-succinate (LDPEG-S), preferably with succinic anhydride (SA), followed by the formation of a reactive ester, preferably with N-hydroxy succinimide (NHS), to form LDPEG-SS, and then reacting of LDPEG-SS with an accessible reactive site on SOD, preferably a primary amine residue on SOD, mainly lysine epsilon amine.

Referring specifically to LDPEG-SOD, the process is as shown:

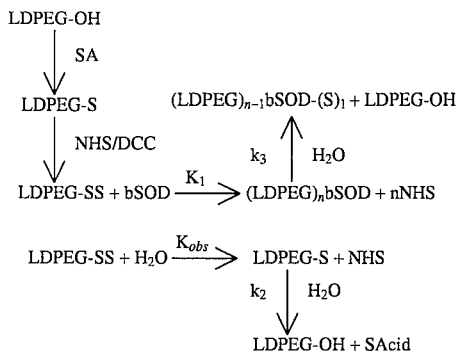

wherein:
LDPEG-OH=low diol $CH_3O$-PEG-OH containing not more than about 10% w/w of HO-PEG-OH LDPEG-SS=low diol $CH_3O$-PEG-$OCOCH_2CH_2COO(C_4H_4NO_2)$ containing not more than 10% of $[(C_4H_4O_2N)OOC—CH_2CH_2COO]_2PEG$ LDPEG-S=low diol $CH_3O$-PEG-$OCOCH_2CH_2COOH$ containing not more than 10% of $[HOOC—CH_2CH_2—COO]_2PEG$ DCC=dicyclohexylcarbodiimide SA=succinic anhydride bSOD=Bovine Superoxide Dismutase NHS=$(C_4H_4NO_2)OH$, N-hydroxysuccinimide $(LDPEG)_n bSOD$=low diol($CH_3O$-PEG-$OCOCH_2CH_2CO)_n$—bSOD $(LDPEG)_{n-1} bSOD$-S=low diol($CH_3O$-PEG-$OCOCH_2CH_2CO)_{n-1}$—bSOD-$COCH_2CH_2COOH$ SAcid=Succinic Acid n=number of low diol PEGs per SOD $K_1$, $K_{obs}$, $k_2$ and $k_3$ are rate constants for the reactions.

LDPEG-SOD is formed by the covalent attachment of activated LDPEG to reactive sites on SOD, primarily reactive amine sites such as epsilon lysine amine sites. The latter are converted to an amide for each LDPEG attached. The resulting LDPEG-SOD product is heterogeneous with respect to both the degree of pegation and the site of attachment of the LDPEG since the reaction may occur at least at any number of available reactive amine sites. In addition, when the LDPEG is bifunctional, i.e., when the activated reagent is derived from LDPEG diol, each end of the LDPEG moiety can potentially react with reactive sites on the protein. The local chemical environment proximal to the protein-S-LDPEG linkage site is essentially independent of the presence of a functional group at the opposite end of the LDPEG chain so that SOD-S-LDPEG-X would, proximal to the SOD-S end of the moiety, be independent of X being $OCH_3$ or OH or O-Succinate or O-S-SOD. In this regard, antibodies raised to SOD-S-LDPEG-X should perceive no differences in the regions proximal to protein in SOD-S-LDPEG versus SOD-S-LDPEG-S-SOD because of symmetry. This would also be true for the species SOD-S from SOD-S-LDPEG versus SOD-S-LDPEG-S-SOD. Indeed, the symmetrical nature of a long chain polyethylene oxide would require that antibodies that recognized the ethylene oxide segment would not be able to differentiate between $CH_3O$-LDPEG-S-SOD and SOD-S-LDPEG-S-SOD. Only the region of variation at the terminus of the polyethylene oxide would present a unique epitope for antibody recognition. Thus it would be expected that antibodies that are raised to a class of compounds comprised of $CH_3O$-LDPEG-S-SOD plus SOD-S-LDPEG-S-SOD would recognize the $CH_3O$-LDPEG end region in a unique fashion, but would not be able to differentiate between the LDPEG-S-SOD region uniquely in $CH_3O$-LDPEG-S-SOD versus SOD-S-LDPEG-S-SOD because of the inherent symmetries involved. Thus, in a system such as the above mixture, were the amount of $CH_3O$-LDPEG-S-SOD to be increased relative to the amount of SOD-S-LDPEG-S-SOD and such a system were then to be exposed to antibodies raised to the former system, an increased response to the $CH_3O$-LDPEG epitope would be expected in the presence of a constant response to the LDPEG-S-SOD epitope by the antibodies.

DETAILED DESCRIPTION OF THE INVENTION

Different molecular weight components in PEG-SOD prepared from high and low diol monomethoxy-PEG were isolated and characterized as follows:

Methods routinely used to characterize the molecular weight of proteins, such as size exclusion chromatography (SEC), ion exchange chromatography (IEC), and polyacrylamide gel electrophoresis (PAGE) are not well suited for PEG modified proteins, since the resulting product is a combination of linear (PEG) and globular (SOD) molecules. In the case of size exclusion chromatography (SEC), the molecular weight values generated are 'apparent', since the columns used are designed to fractionate globular materials, and the presence of an extended linear molecule on the protein surface makes the entire molecule appear larger than it really is. Application of IEC to PEG modified proteins is not very useful, since the extended structure of the PEG groups does not allow intimate interaction of the protein surface with the solid phase. For native PAGE, the migrational characteristics are influenced by the charge and the size of the total molecule, resulting in smeared bands for PEG-SOD after staining. Sample preparation for SDS-PAGE is quite harsh (SDS treatment in boiling water), which results in the ester bonds in the linkage between the SOD and PEG being partially hydrolyzed, resulting in gels which possess no resolution and extensive smearing. Also, silver staining is not applicable for pegated proteins, probably due to the interference of the surface staining of the protein by the PEG groups, and staining has to rely totally on Coomassie. We have conducted a study to fractionate the different molecular weight species of PEG modified SOD and characterize them via Size Exclusion Chromatography (SEC), photon correlation spectroscopy (PCS), Differential scanning Calorimetry (DSC), high temperature treatment and base hydrolysis.

Materials and Methods

1. High and Low Diol PEG-SOD

SOD was obtained from DDI, Inc. (Mountainview, Calif.) and pegated using reagents derived from methoxypoly(ethylene glycol) obtained from Union Carbide Corporation and comprised of MPEG with high (14–17%) and with low diol (2.3%) content. Nominal average molecular weights are denoted by subscripts.

2. Size Exclusion HPLC (SEHPLC)

The solid phase consisted of a Superose 6 Prep Grade HR 10/30 column (Pharmacia, Inc.). The mobile phase consisted of 50 mM phosphate buffer, pH 6.2 containing 150 mM sodium chloride. The flow rate was 0.7 ml/min and the detector was set at 214 nm.

Figure 1A:
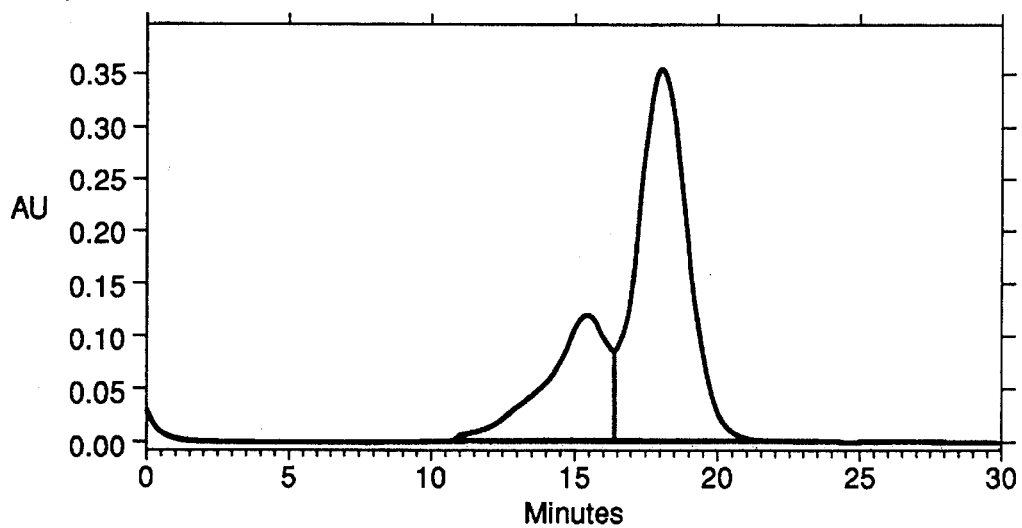
FIG. 1A represents size Exclusion High Performance Liquid Chromatography of high diol PEG-SOD.
Figure 1B:
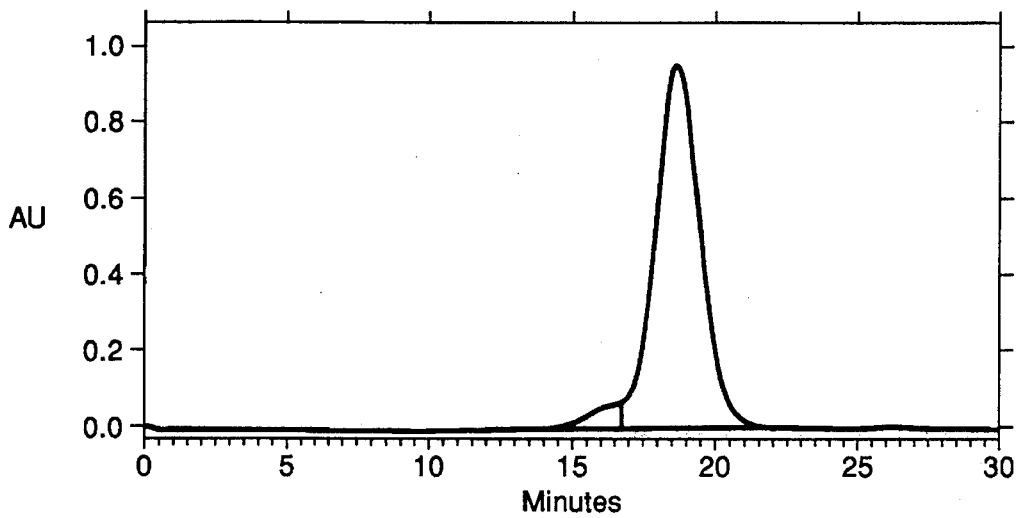
FIG. 1B represents size Exclusion High Performance Liquid Chromatography of low diol PEG-SOD.
Figure 1C:
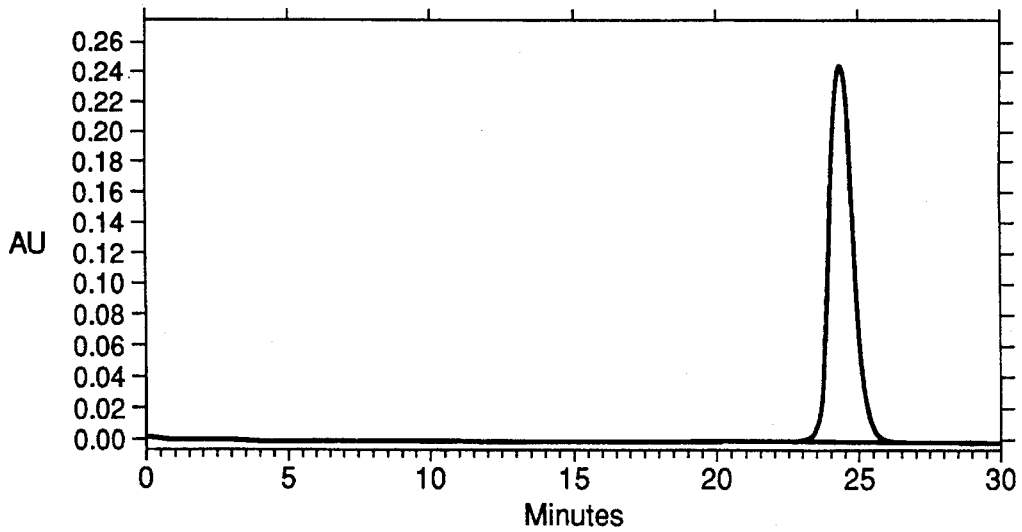
FIG. 1C represents size Exclusion High Performance Liquid Chromatography of Native SOD.

Samples of SOD and PEG-SOD produced with either high or low diol MeO-PEG$_{5,000}$ were injected onto a Superose HR10/30 column (FIG. 1). SOD (FIG. 1C) possessed a retention time of approximately 24 minutes corresponding to a molecular weight of 32,000 (calculated from retention times of molecular weight standards). PEG-SOD made with high diol PEG-SS (FIG. 1A) produced a bimodal elution profile with the main peak (LMW) at 18.0 minutes (apparent molecular weight: 400,000) and an early eluting peak (HMW) at 15.4 minutes (apparent molecular weight: 1,000,000), along with some material eluting in the void volume of the column (exclusion limit: 40 million MW). The early eluting peak (HMW) for the high diol PEG-SOD made up to 30% of the total protein based on peak area. PEG-SOD prepared with low diol PEG-SS (FIG. 1B) produced a bimodal elution profile with a high molecular weight component comprising less than 6% of the total protein based on peak area. The retention time for the low diol PEG-SOD main peak (LMW) was at 18.6 minutes (apparent molecular weight: 370,000) and that of the early eluting peak (HMW) was at 16.7 minutes (apparent molecular weight: 550,000).

As shown in FIG. 1C, SOD elutes with a retention time of 24.3 minutes which corresponds to a calculated molecular weight of 34,000. When SOD is covalently coupled to high diol PEG$_{5,000}$, the overall molecular weight of the resulting material increases. The PEG-SOD prepared with high diol MeO-PEG$_{5,000}$ possesses a bimodal distribution indicating product heterogeneity (FIG. 1A). The two main peaks elute at 15.4 and 18.0 minutes, comprising 30 and 70% of total protein content based on peak area, respectively. The early eluting peak (HMW, 15.4 minutes) possesses an 'apparent' calculated molecular weight of approximately 1 million. The HMW signal also has some material which elutes in the void volume of the column (10 minutes) corresponding to an 'apparent' molecular weight in excess of 40 million (VHMW). The material from the late eluting peak (LMW, 18.0 minutes) has an 'apparent' calculated molecular weight of approximately 400,000. The true molecular weight of the modified protein cannot be determined by this type of chromatography, since the column is measuring 'apparent' molecular weight as the solid phase is solely designed to resolve globular proteins and not linear ones. The presence of the linear PEG molecule attached to the SOD surface imparts a highly extended structure to the overall molecule, making the determination of molecular weight by SEHPLC qualitative at best.

Figure 2:
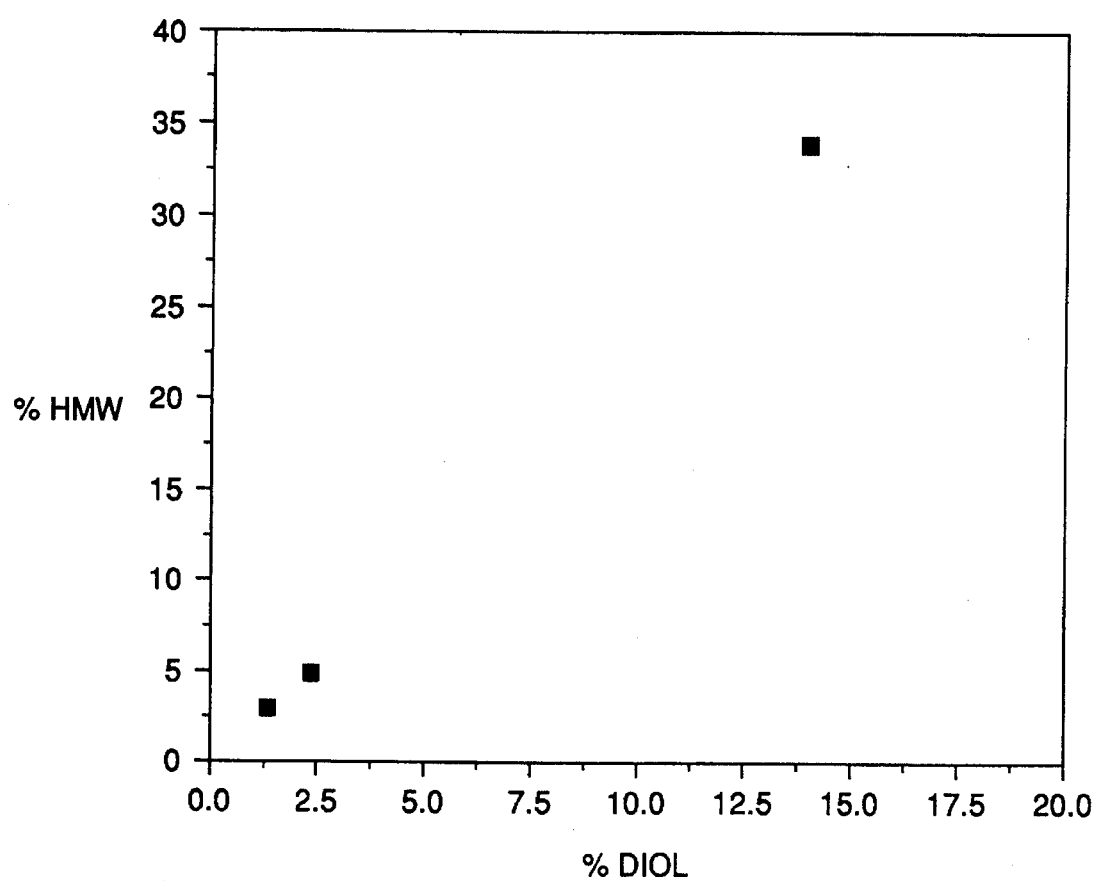
FIG. 2 represents the effect of diol content in PEG-SS and amount of high molecular weight (HMW) PEG-SOD produced.

When PEG-SOD is prepared from low diol methoxy-PEG$_{5,000}$, the elution profile is still bimodal (FIG. 1B), but the HMW signal decreases to approximately 4.8% of the total protein content. Also, the retention times of the HMW and LMW peaks are now observed to be slightly longer (16.6 and 18.6 minutes for HMW and LMW, respectively) as compared to the high diol PEG-SOD preparation. This observation, along with the fact that the low diol preparation does not possess any VHMW material appearing in the void volume of the column, indicates that lowering the diol content to 2.3% (from 14–17%) significantly reduces the formation of the high molecular weight material. It is believed that the VHMW and HMW materials are primarily formed due to presence of the bis-SS-PEG (formed from the diol component in the methoxy-PEG) which acts as a crosslinking agent between proximally oriented lysine groups on separate SOD molecules during pegation. If this hypothesis is correct, the extent of HMW material formed should be proportional to the diol content of the MeO-PEG starting material. In FIG. 2 is shown a plot of the percent HMW signal versus percent diol for three lots of PEG-SOD, (with 14% diol, 2.3% diol and 1.3% diol). As seen in the range of diol content studied, there is a nearly linear increase in percent HMW with diol content supporting the hypothesis that the extent of HMW material formed in the final product is related to the diol content of MeO-PEG. Studies indicate that while freshly made PEG-SOD from the high diol PEG-SS contains approximately 30% HMW material, after 2 years storage at 5° C., the HMW signal decreases to approximately 10% indicating that the HMW material is labile and converts to a lower molecular weight material on storage.

3. Low Pressure Size Exclusion Chromatography (LPSEC)

An XK 50/100 column packed with 1.56 liters of Superose 6 (Prep Grade Pharmacia, Inc.) was used. The mobile phase consisted of 50 mM phosphate buffer, pH 6.2, containing 500 mM sodium chloride. The flow rate was 2 ml/min and the detector (Pharmacia, Inc. ) was set at 280 nM. Fractions (12 ml) were collected using a Frac-100 Fraction collector (Pharmacia, Inc.) and analyzed by SEHPLC and pooled.

(a) Fractionation of Components from high diol PEG-SOD

Figure 3:
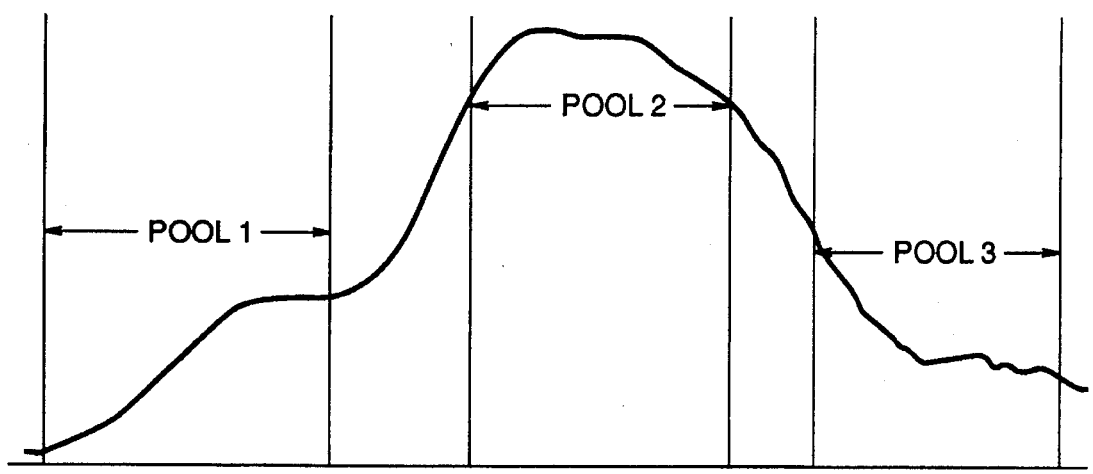
FIG. 3. represents the elution profile of high diol PEG-SOD from Superose 6 Prep. Grade Column using Low Pressure Size Exclusion Chromatography (LPSEC)

Twenty-five ml of high diol PEG-SOD at 35.3 mg/ml was applied to a 1.59 liter Superose 6 Prep Grade column. The material produced the elution profile as shown in FIG. 3. SEHPLC analysis of collected samples indicated that fractions 15 through 30 represent Pool 1 (HMW), fractions 40 through 60 represent Pool 2 and fractions 70 through 90 represent Pool 3 (LMW). The SEHPLC elution profiles of the pools are shown in FIG. 4.

(b) Fractionation of Components from Low Diol PEG-SOD

Figure 5:
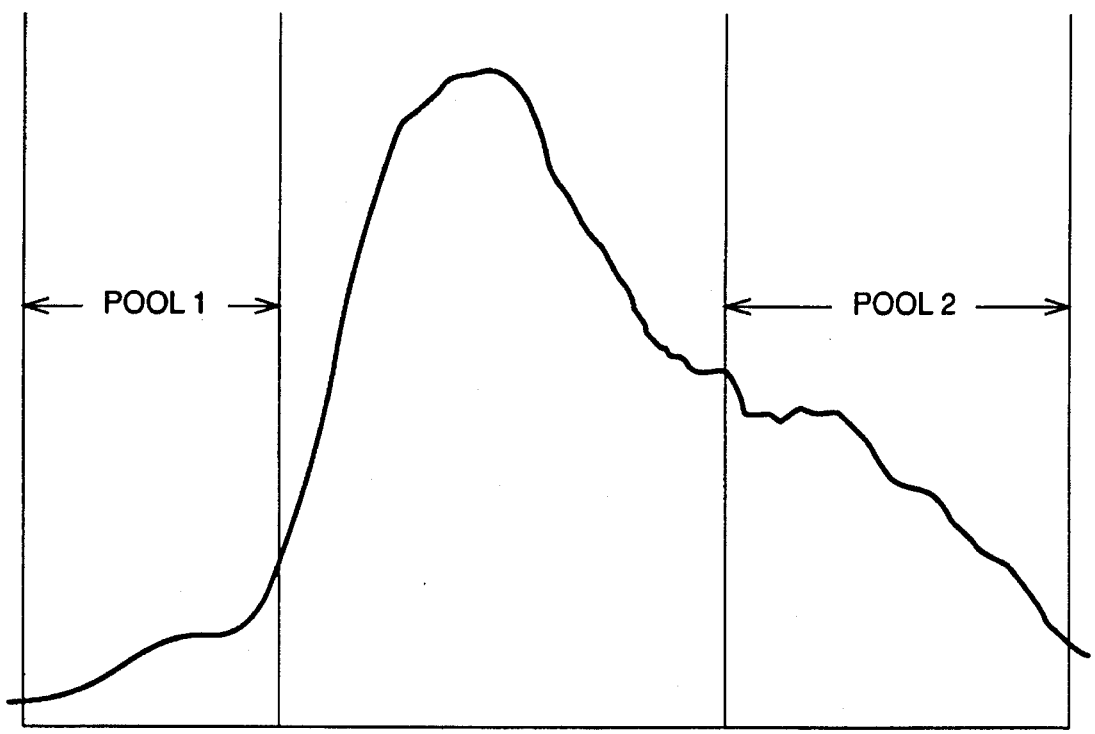
FIG. 5 represents the elution profile of low diol PEG-SOD from Superose 6 Prep Grade Column using Low Pressure Size Exclusion Chromatography (LPSEC)
Figure 6A:
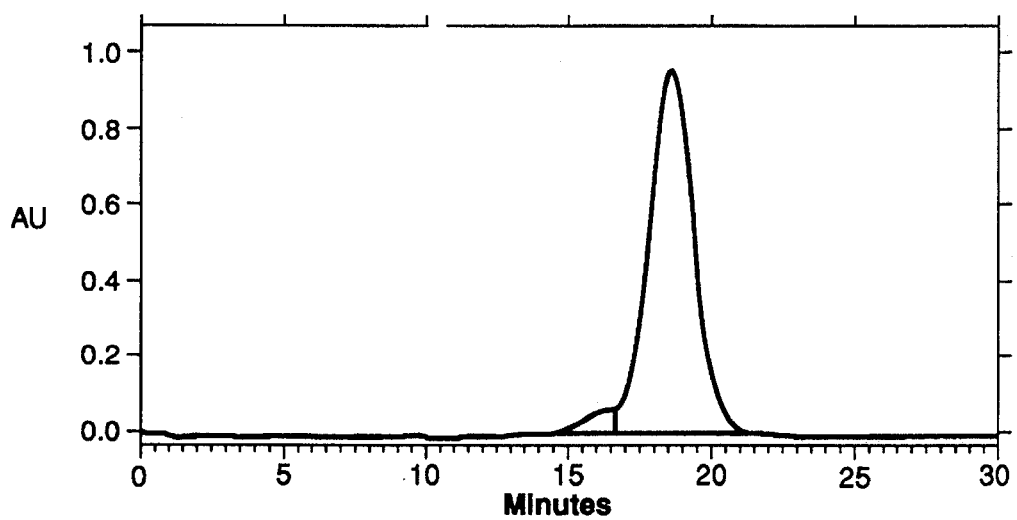
FIG. 6 represents Size Exclusion High Pressure Liquid Chromatography (SEHPLC) profiles of the pools obtained in FIG. 5.
Figure 6B:
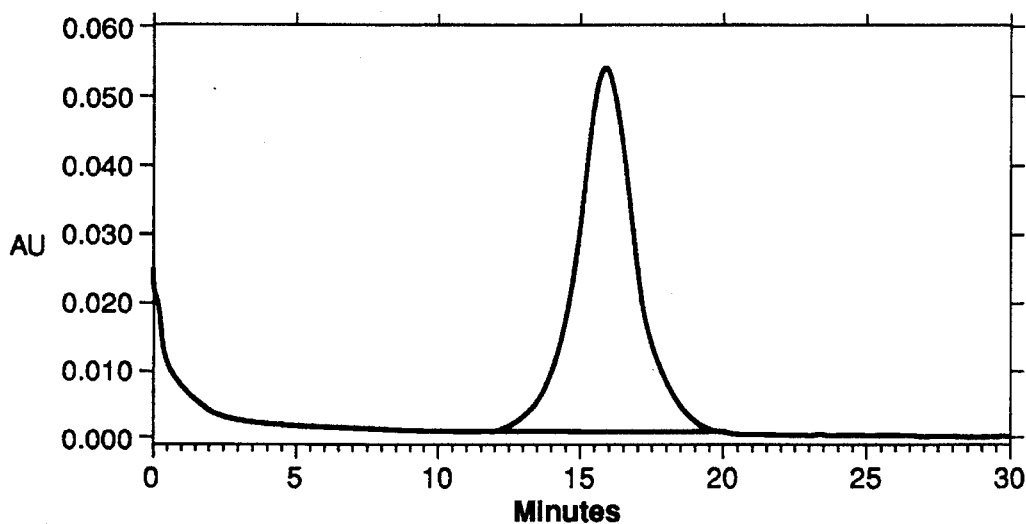
Figure 6C:
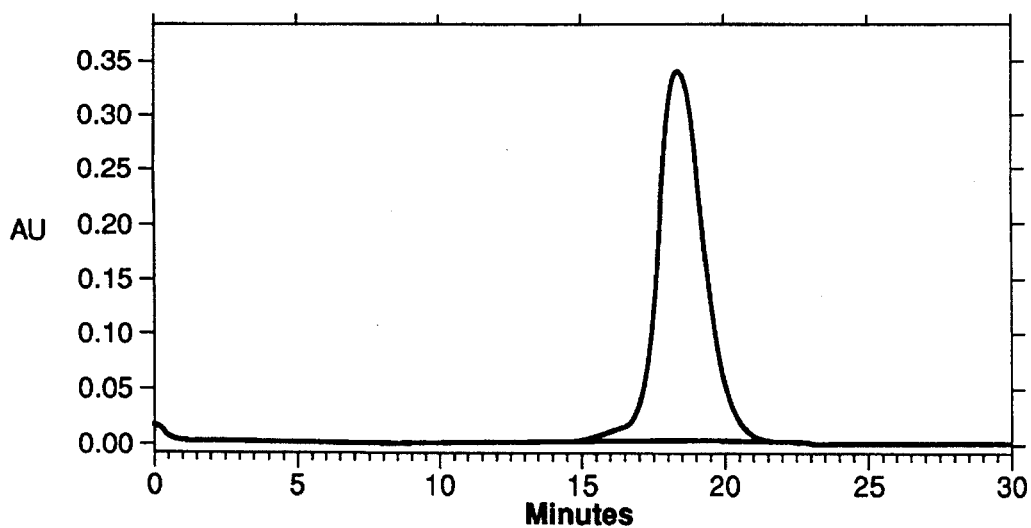

Twenty-five ml of low diol PEG-SOD at 28 mg/ml was applied to the 1.59 liter Superose Prep Grade 6 column. The material produced the elution profile as seen in FIG. 5. SEHPLC analysis of collected samples indicated that fractions 5 though 15 represent Pool 1 (HMW), fractions 50 through 70 represent Pool 2 (LMW). The elution profiles of the pools on analytical SEHPLC are shown in FIG. 6.

Fractionating the high diol PEG-SOD preparation on a Superose 6 Prep Grade column produces an elution profile (FIG. 3), very similar to that observed with the SEHPLC system used in this study (FIG. 1A). The resulting HMW pool (FIG. 4B) was not completely free of all LMW material, probably due to the resolving capacity of the Superose 6 column. Also, LMW from the high diol PEG-SOD preparation (FIG. 4D) had to be fractionated twice because the first run still possessed over 15% HMW in the LMW pool. When the material was re-run, it was possible to decrease the HMW signal to 9.6% of the total protein content. When the fractionated HMW and LMW were tested for enzyme activity, both were found to be active (data not shown). In terms of specific activity, there was no detectable inactivation of the HMW material when compared to unfractionated PEG-SOD or LMW material. It appears from these studies (and also as reported by Veronese et al, *Journal of Controlled Release,* 10: 145–154 (1989)) that the observed decrease in enzyme activity of SOD upon modification with high or low diol PEG-SS is related to the amino groups which are modified, thereby changing the charge on the enzyme surface. The size modification induced by the diol PEG (i.e., formation of HMW) does not lead to any significant decrease in activity. Whether the HMW material is significantly less active than other fractions in an absolute sense is still a point for speculation, since the variability in determining protein concentrations and enzyme activity introduce considerable error into the data.

When PEG-SOD prepared from low diol PEG-SS is fractionated on the Superose 6 Prep grade column, it produces an elution profile as shown in FIG. 5. As seen with the high diol PEG-SOD, the low diol PEG-SOD produced an elution profile which closely resembles chromatograms observed with the analytical SEHPLC system. The loading conditions for the low diol PEG-SOD were almost identical to that of the high diol PEG-SOD, but the resulting HMW and LMW pools (FIGS. 6B and 6C) were almost free of cross-contamination providing retention times of 15.9 and 18.4 minutes, respectively. It should be noted that the main peak (LMW) produced in both high and low diol preparations had very similar retention times (high diol: 18.0 minutes, low diol: 18.6 minutes), indicating that the principal product, regardless of diol content, is similar.

4. Photon Correlation Spectroscopy (PCS)

A Malvern Model 4700 PCS with a 3 watt Spectraphysics laser set at 488 nm was used for the determination of molecule sizes. The temperatures of the samples and reference solution were kept at 25° C. SOD (in deionized water) and PEG-SOD (from high and low diol preparations) were at concentrations of 10 mg/ml in 50 mM phosphate buffer, pH 6.2, 150 mM sodium chloride. HMW and LMW samples were at a concentration of 10 mg/ml in pH 6.2, 50 mM phosphate buffer containing 500 mM sodium chloride. Samples of (2 ml) were filtered through a 0.2 μm, 25 mm Millipore GV filter into clean cuvettes and allowed to equilibrate for 15 minutes before each measurement.

SOD (used as a reference) was observed to have a molecular size of 3 nm which is in good agreement with literature reported values, while unfractionated high diol PEG-SOD had a molecular size of 14 nm. HMW & LMW materials fractionated from high diol PEG-SOD demonstrated molecular sizes of 22 and 12 nm, respectively. Unfractionated low diol PEG-SOD generated an average molecular size of 11 nm.

5. Differential Scanning Calorimetry (DSC)

A microcal MC-2 Differential Scanning Calorimeter was used with a starting temperature of 36° C., a scan rate of 60° C./hr and an ending temperature of 105° C. SOD and Pool 1 concentrations were at 5 mg/ml while the concentration of Pool 3 (LMW) was at 6.9 mg/ml (both Pool 1 and 3 were fractionated from high diol PEG-SOD). All samples were in pH 6.2, 50 mM phosphate buffer containing 500 mM sodium chloride. The samples and reference buffer were filtered through a 0.2 μm filter and allowed to equilibrate at 35° C. for 30 minutes before the initiation of scans.

Figure 7:
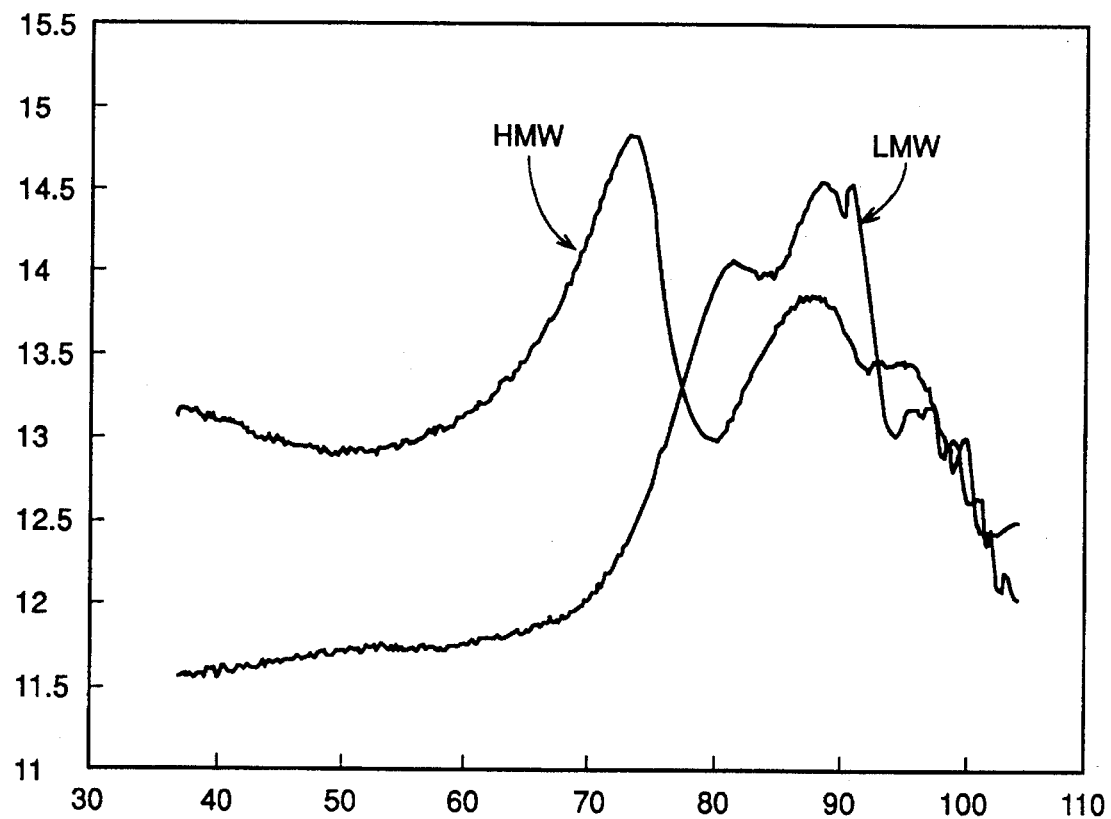
FIG. 7 represents melting temperature values of Pools 1 and 3 (LMW) fractions of high diol PEG-SOD obtained in FIG. 5.
Figure 8A:
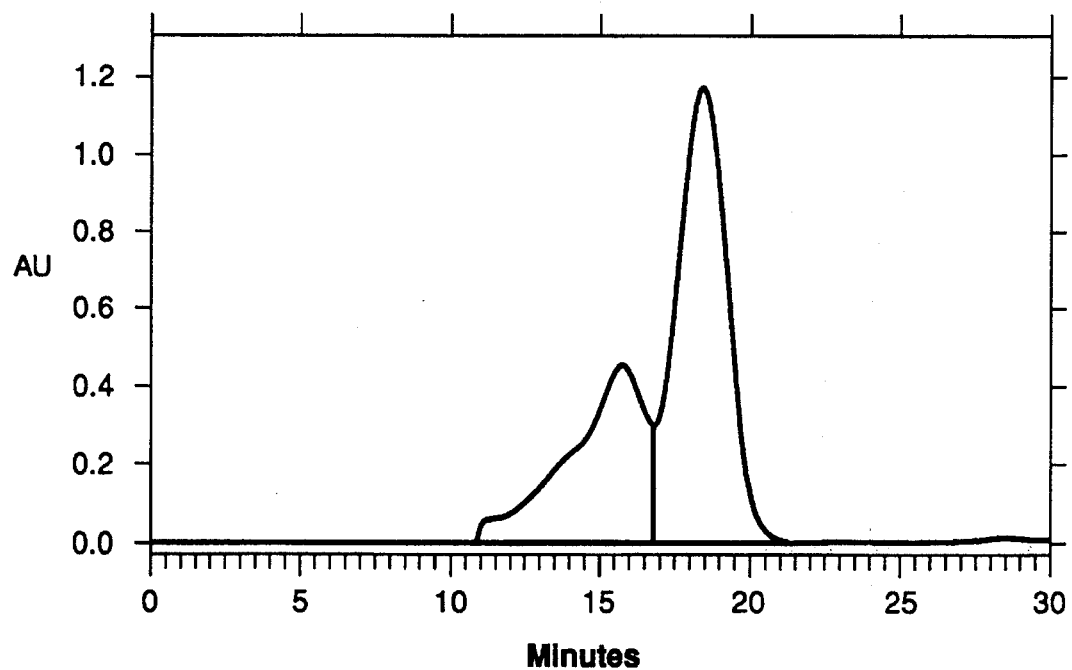
FIG. 8 represents Size Exclusion High Pressure Liquid Chromatography (SEHPLC) of unfractionated high diol PEG-SOD, Pool 1 (HMW), Pool 2 and Pool 3 (LMW) obtained in FIG. 3 at the start of the study and after 2 weeks exposure at 50° C.
Figure 8B:
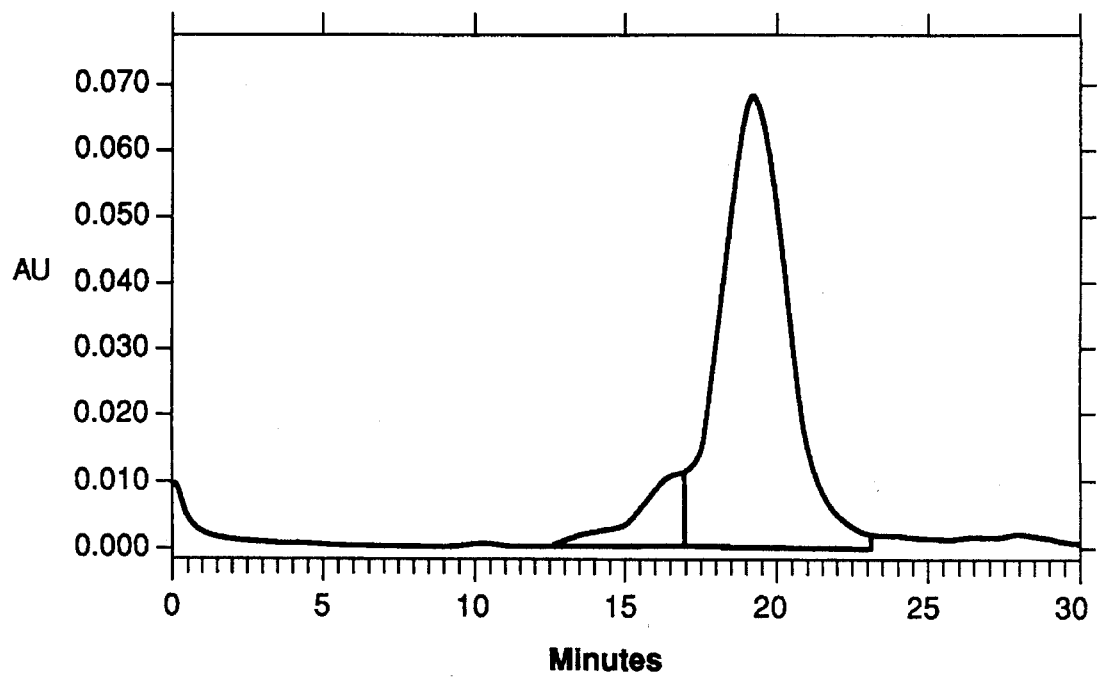
Figure 8C:
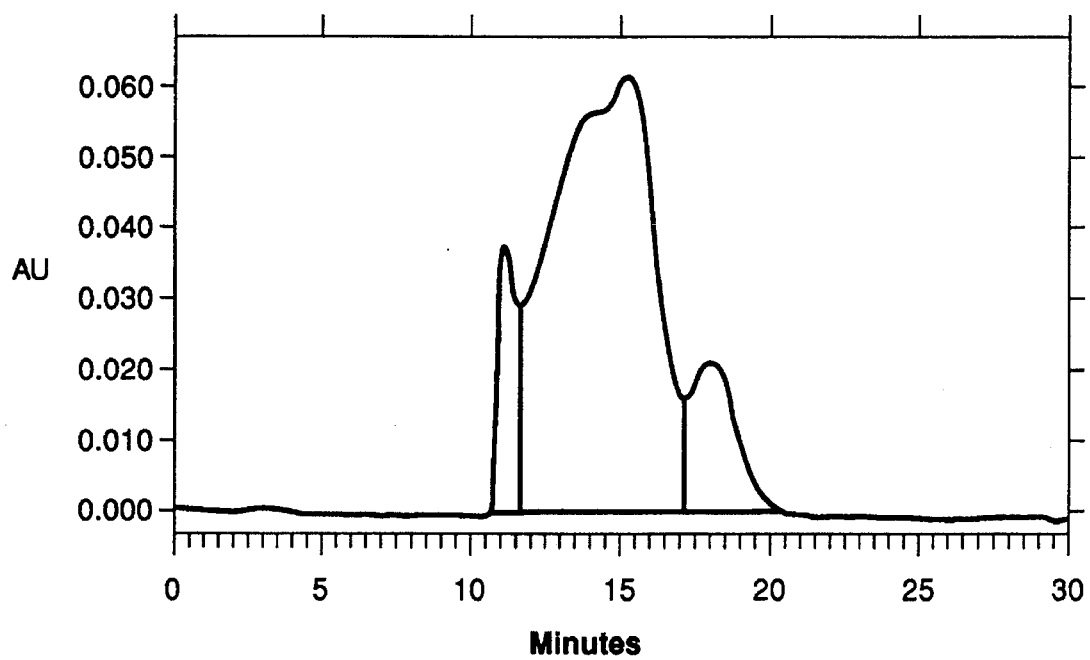
Figure 8D:
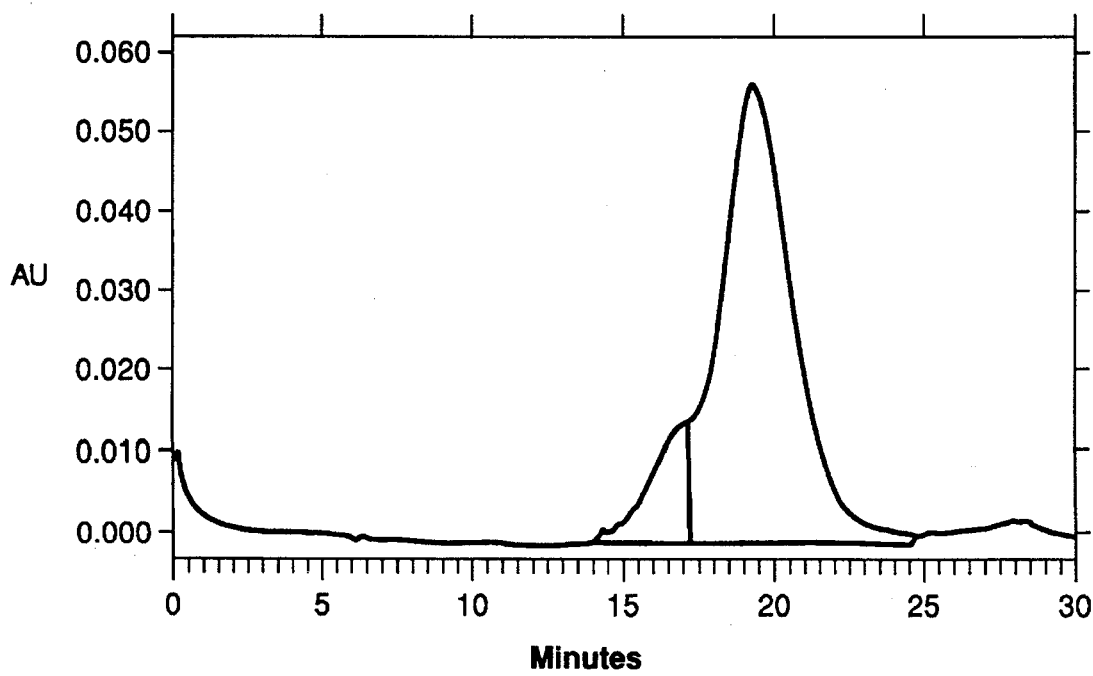
Figure 8E:
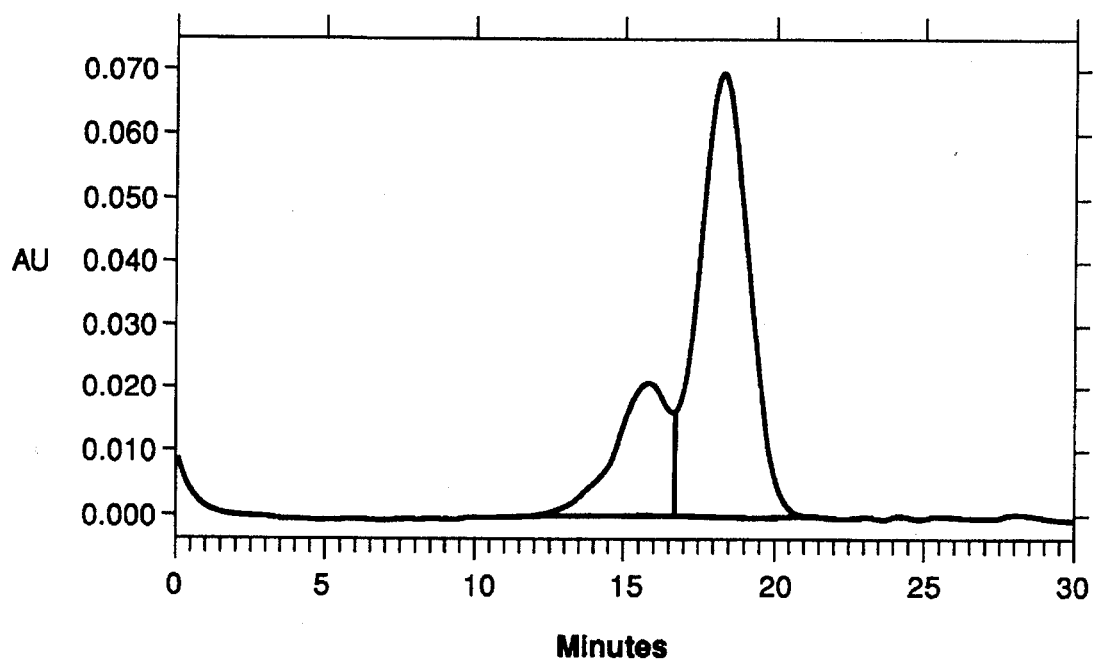
Figure 8F:
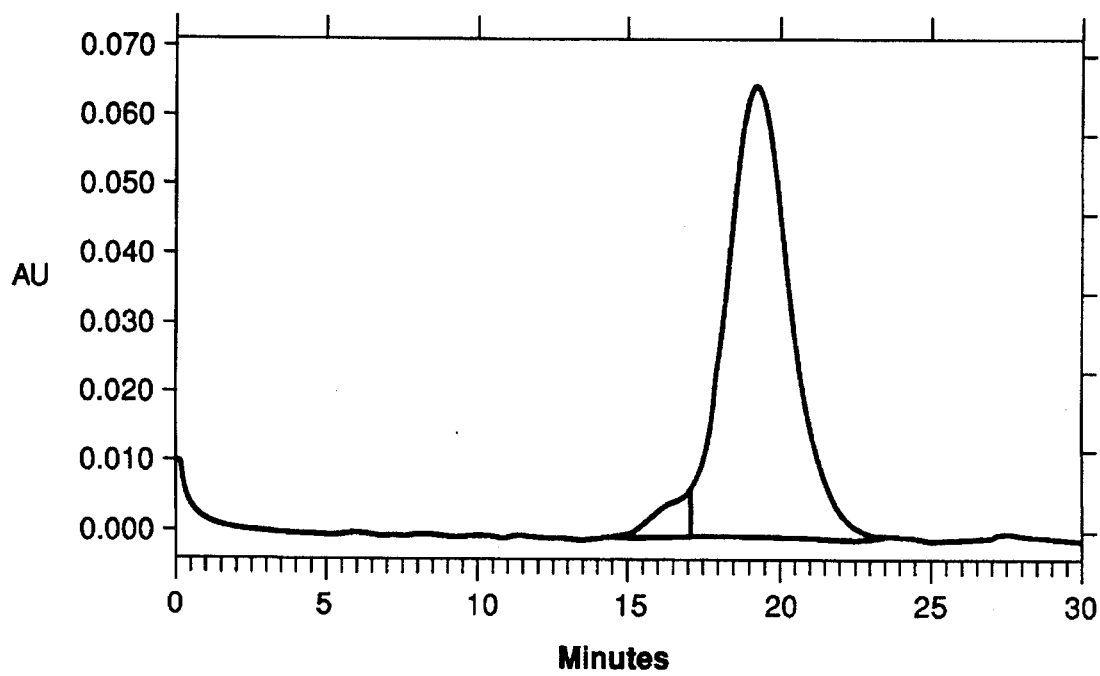
Figure 8G:
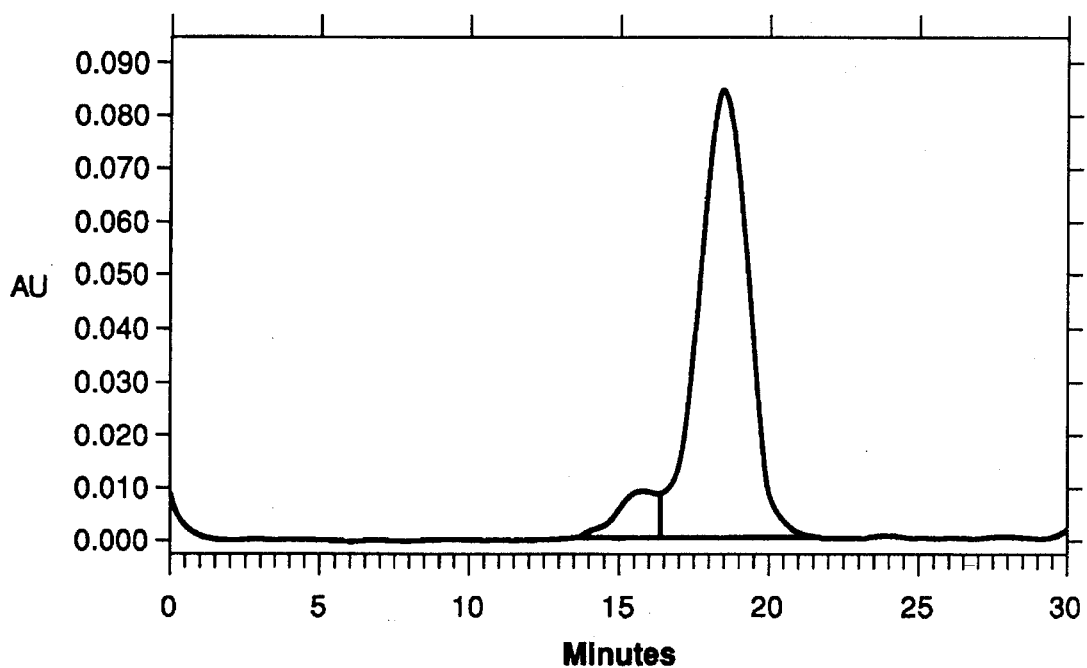
Figure 8H:
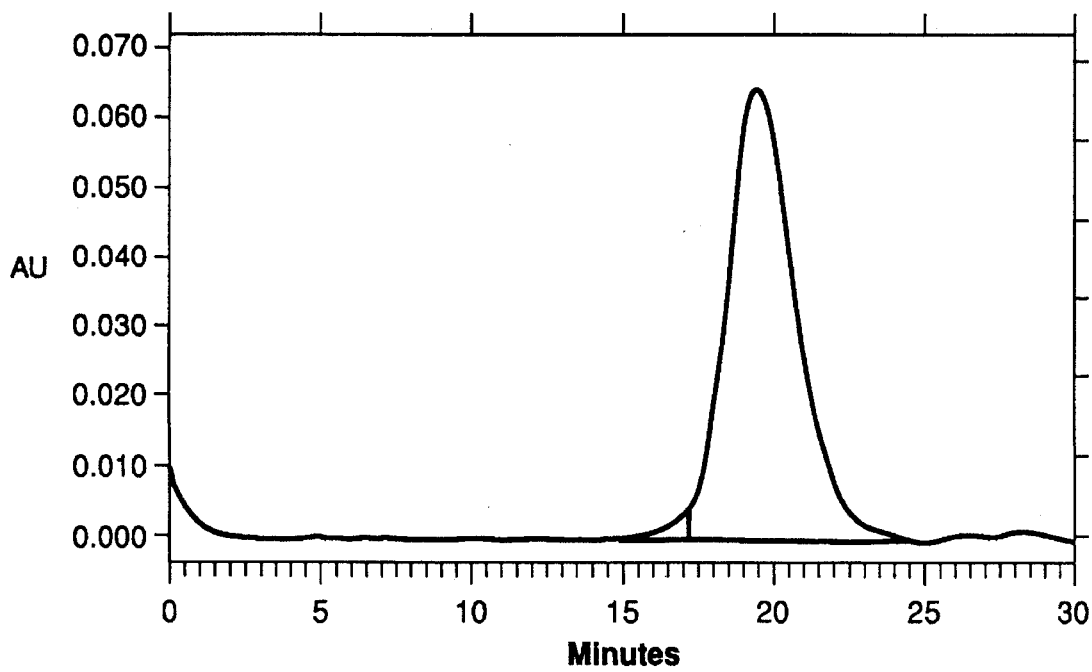

Pool 1 and Pool 3 (LMW) isolated by fractionation of high diol PEG-SOD had $T_m$ (melting temperature) values of approximately 71° and 91° C., respectively (FIG. 7), while SOD (used as a reference, data not shown) possessed a melting temperature of 93° C.

6. Sterile/Pyrogen-Free Gel Filtration (S/PF GF)

The same column apparatus as described in Section 3 was used. The column was pre-washed with 2 liters of 0.1M sodium hydroxide and equilibrated with at least 10 liters of buffer prefiltered through a 0.2 μm filter and tested to be free of endotoxins (using a quantitative chromogenic LAL assay, Whittaker Bioproducts, Inc., P/N 50-647-U). After the column eluent endotoxin level was found to be less than 1 EU/ml, the elution and pooling conditions outlined in Section 3 were used.

Figure 11:
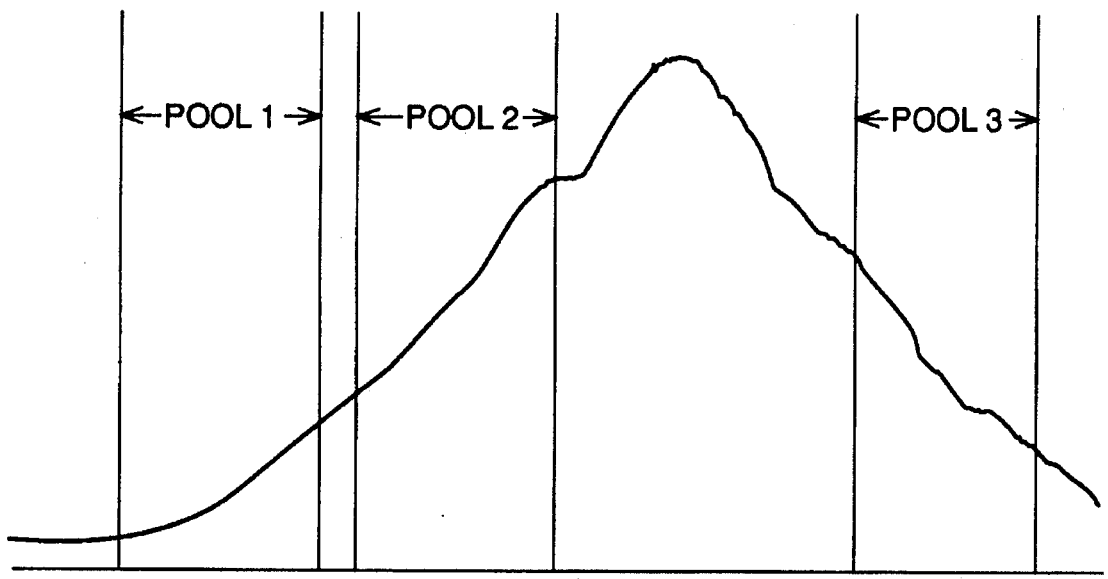
FIG. 11 represents sterile/pyrogen-free Superose 6 Prep Grade fractionation of high diol PEG-SOD.
Figure 12A:
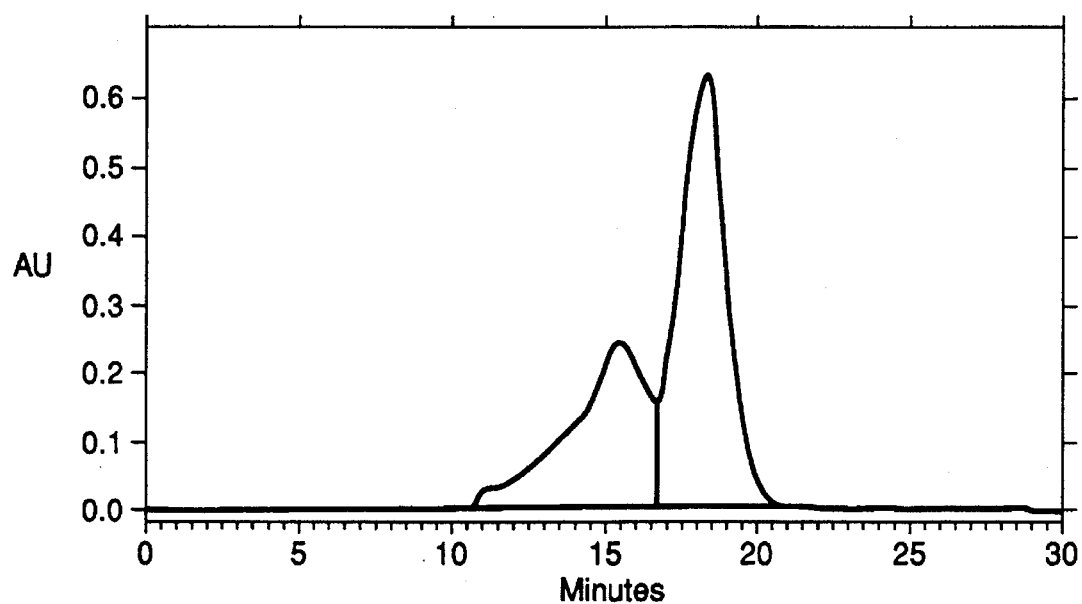
FIG. 12 represents chromatograms of fractions shown in FIG. 11.
Figure 12B:
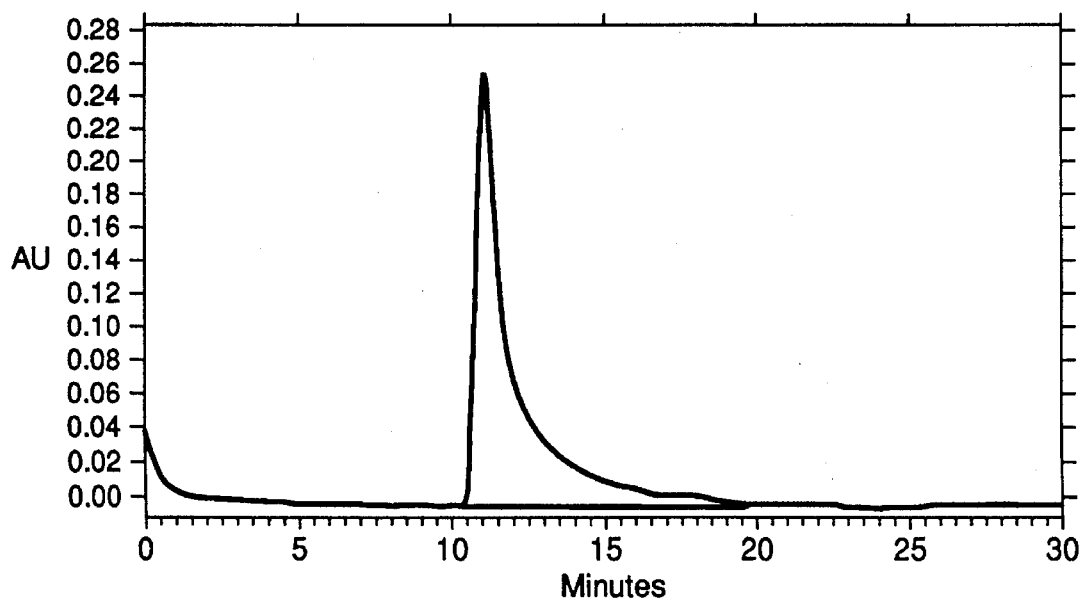
Figure 12C:
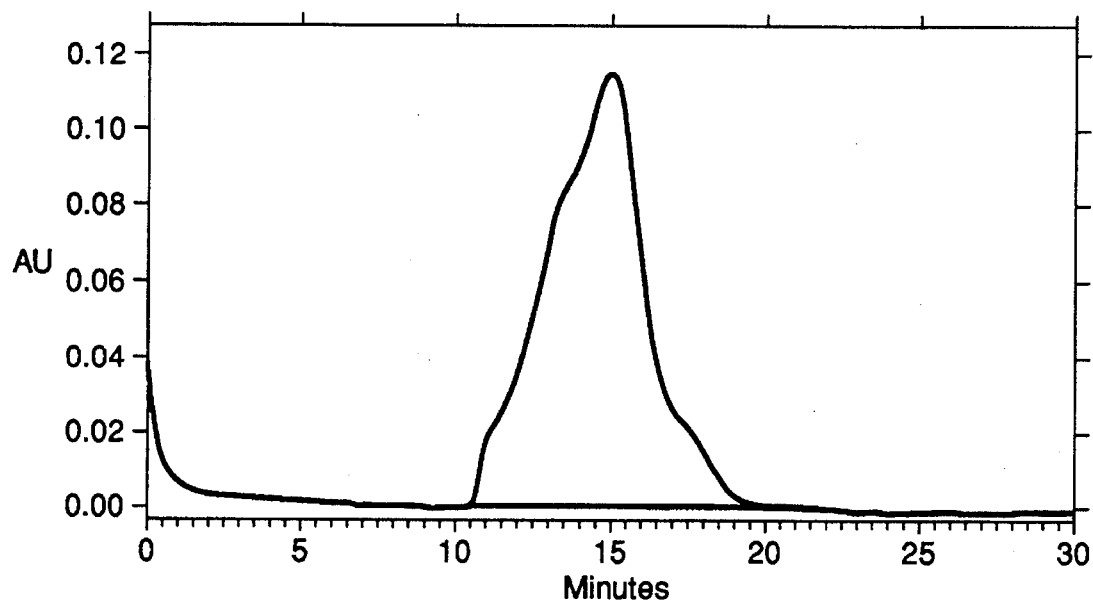
Figure 12D:
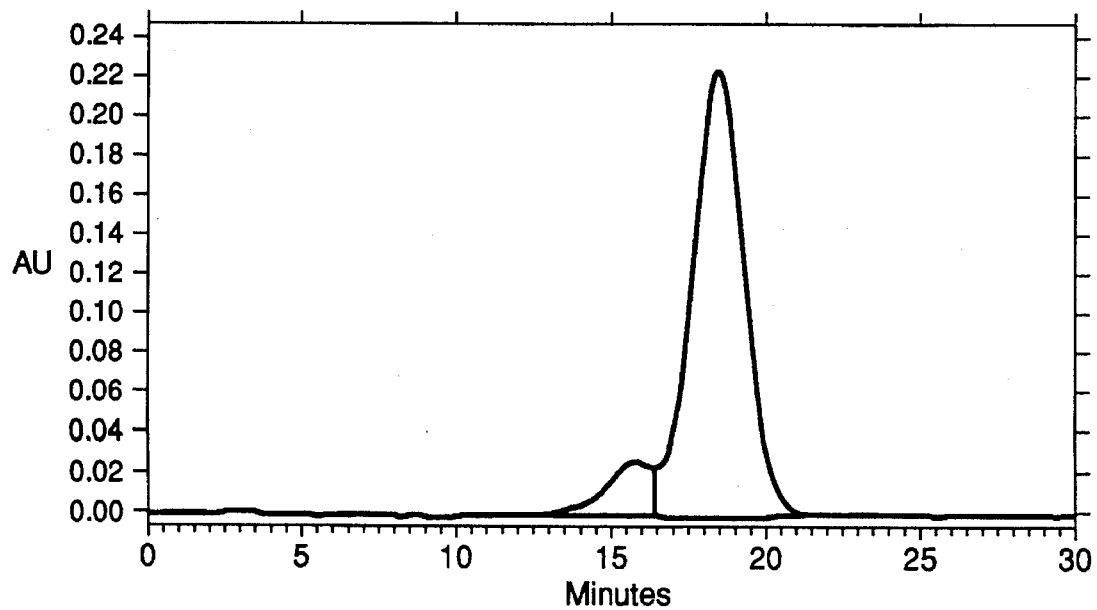

Twenty-five mls of high diol PEG-SOD applied to a depyrognated 1.56 liter Superose 6 Prep Grade column produced the elution profile shown in FIG. 11. Pooling of fractions after analytical SEHPLC and rechromatographing samples provided the chromatograms shown in FIG. 12, (Pool 1 being very High Molecular Weight (VHMW)), Pool 2 High Molecular Weight (HMW) and Pool 3 Low Molecular Weight (LMW). The recovery (rag of protein) and endotoxin content of the respective fractions are shown in Table 1.

TABLE 1

Sterile/Pyrogen Free Gel Filtration
Recovery of Different Molecular Weight Components
from High Diol PEG-SOD

| Pool | Sample Name | MG/ML | ML | MG | EU/ML | EU/MG |
|---|---|---|---|---|---|---|
| 1 | VHMW | 1.55 | 4 | 6.2 | 25 | 16 |
| 2 | HMW | 4.65 | 14 | 65 | 1 | 0.1 |
| 3 | LMW | 22.2 | 11.5 | 255 | 360 | 16 |

7. High Temperature Treatment

Fractionated material from high diol PEG-SOD, as well as unfractionated high diol PEG-SOD were adjusted to 2 mg/ml in phosphate/salt buffer and sterile filtered. The samples, in glass vials, were then stressed at 4°, 22°, 30°, 40° and 50° C. temperature stress conditions. Samples were analyzed by SEHPLC at predetermined time intervals.

SEHPLC chromatograms of unfractionated high diol PEG-SOD, Pool 1 (HMW), Pool 2 and Pool 3 (LMW) obtained in FIG. 3 at the start of the study and after 2 weeks exposure at 50° C. are shown in FIG. 8.

Figure 4A:
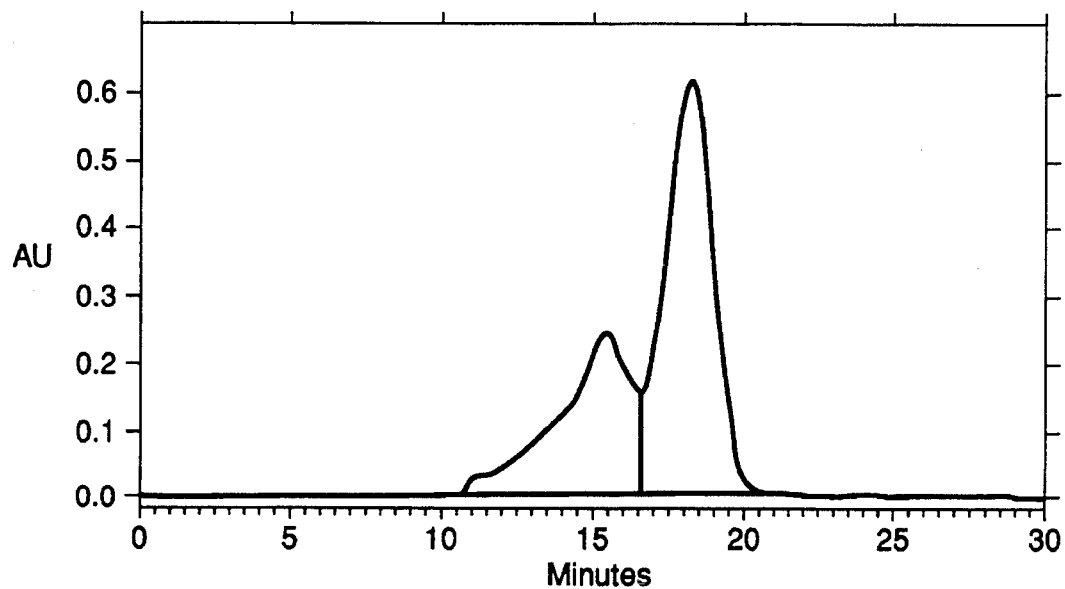
FIG. 4 represents Size Exclusion High Pressure Liquid Chromatography (SEHPLC) profiles of the pools obtained in FIG. 3.
Figure 4B:
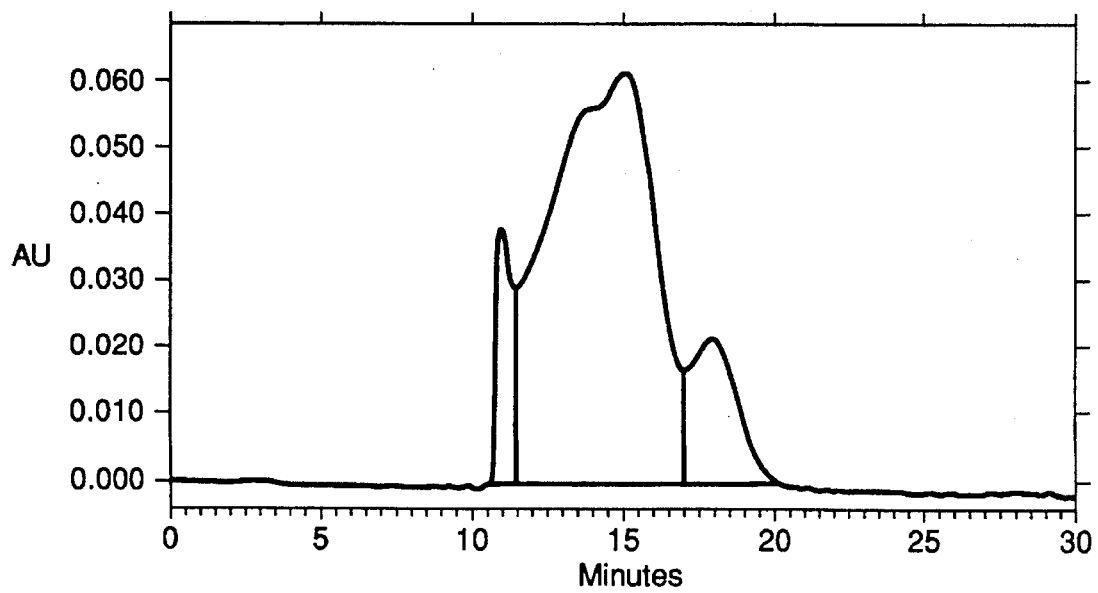
Figure 4C:
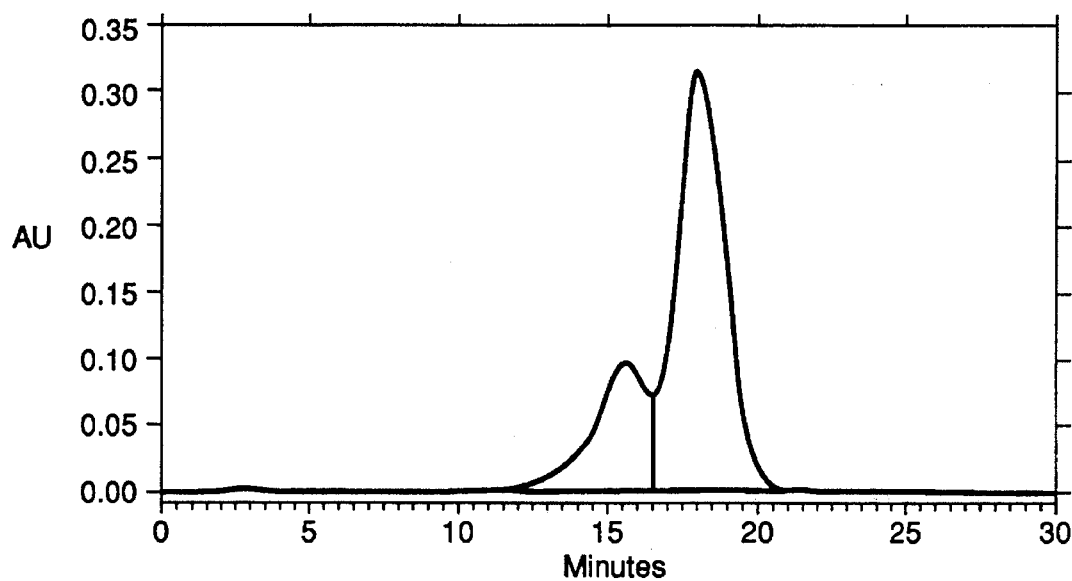
Figure 4D:
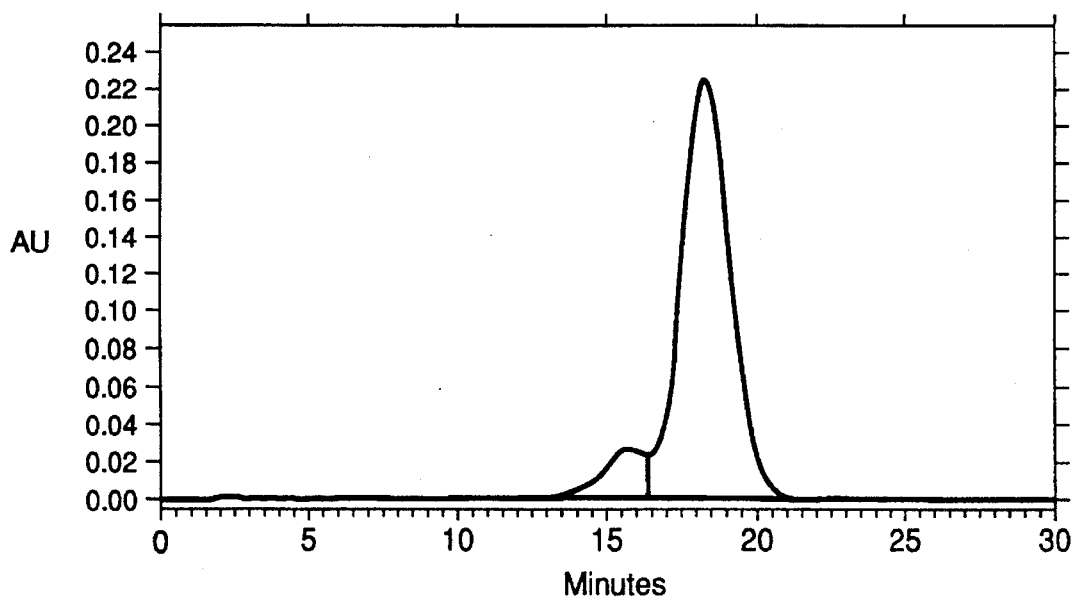

As seen from the thermograms on the HMW and LMW compositions (FIG. 7), the HMW material has a much lower melting point (71° C. as compared to 91° C.) indicating that the HMW material is significantly more heat labile. This may explain the conversion of the HMW material to LMW on storage even under refrigerated conditions. The appearance of secondary peaks in both thermograms is probably due to the presence of contaminating LMW in the HMW sample and HMW in the LMW sample (FIGS. 4A and D).

Subjecting the high diol PEG-SOD, HMW, Pool 2 and LMW samples to 50° C. treatment for two weeks has profound effects on the molecular integrity of the HMW material as evidenced by the SEHPLC signal (FIG. 8). As can be seen for high diol PEG-SOD (FIGS. 8A and 8B), the HMW peak decreases from over 30% of the total protein content to less than 10%, while the retention time of the main peak increases from 18.3 to 19.1 minutes. For the fractionated HMW sample, the 50° C. treatment completely disrupts the original structure of the material and produces an elution profile which closely resembles PEG-SOD prepared from high diol MeO-PEG that has been stored for 2 years at 4° C. (data not shown). The main peak for 50° C. treated HMW elutes at 19.3 minutes, and comprises almost 90% of the total content (FIGS. 8C and D). Similar effects can be observed on Pool 2 and LMW fractions, where the HMW signal practically vanishes. Overall, the data from differential scanning calorimetry and the 50° C. thermal treatment indicate that the HMW material is heat labile and essentially unstable. These observations can be extrapolated to storage at 4° C., expecting that the HMW signal will decrease with time.

8. Base Hydrolysis

HMW and LMW samples as well as unfractionated high diol PEG-SOD, were subjected to base hydrolysis (pH range 10.8–12.02). The pH of 'the solutions was adjusted using 0.1M sodium hydroxide and samples incubated at room temperature for 2 hours. The samples were then chromatographed using SEHPLC for protein determination (as outlined in Section 1) using SOD and succinyl-SOD samples as reference. Free PEG was determined using the HPLC procedure outlined in Section 6.

Protein Component: The elution profiles of samples of high diol PEG-SOD subjected to base hydrolysis in the pH range 10.5 to 12.3 (in increments of 0.3 pH unites) are shown in FIG. 9 (with SOD and Succinyl-SOD as references).

Figure 10A:
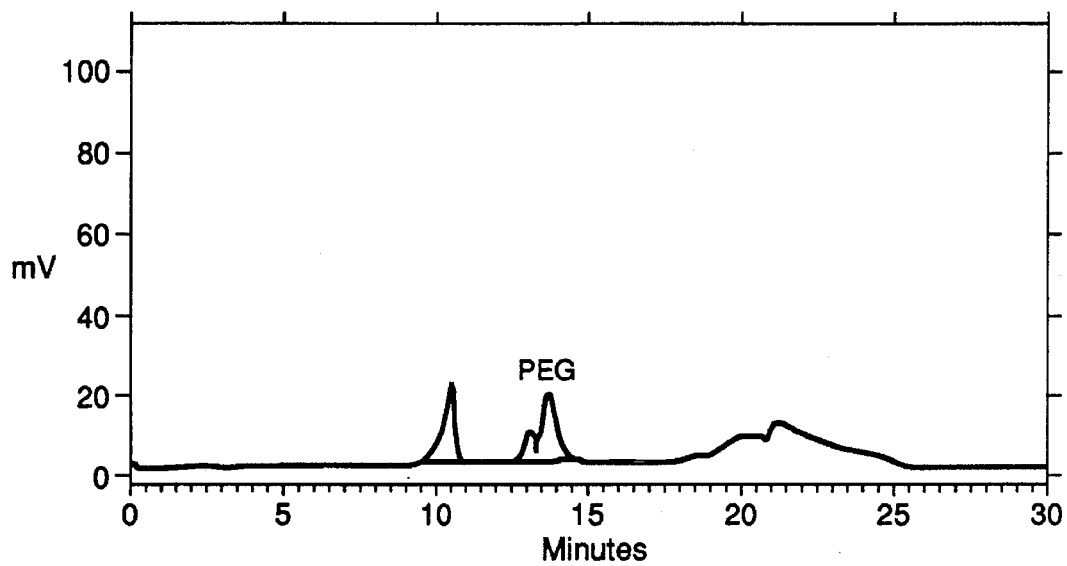
FIG. 10 represents the elution profiles of PEG products from base hydrolysis of high diol PEG-SOD (HMW) and low diol PEG-SOD (HMW and LMW)
Figure 10B:
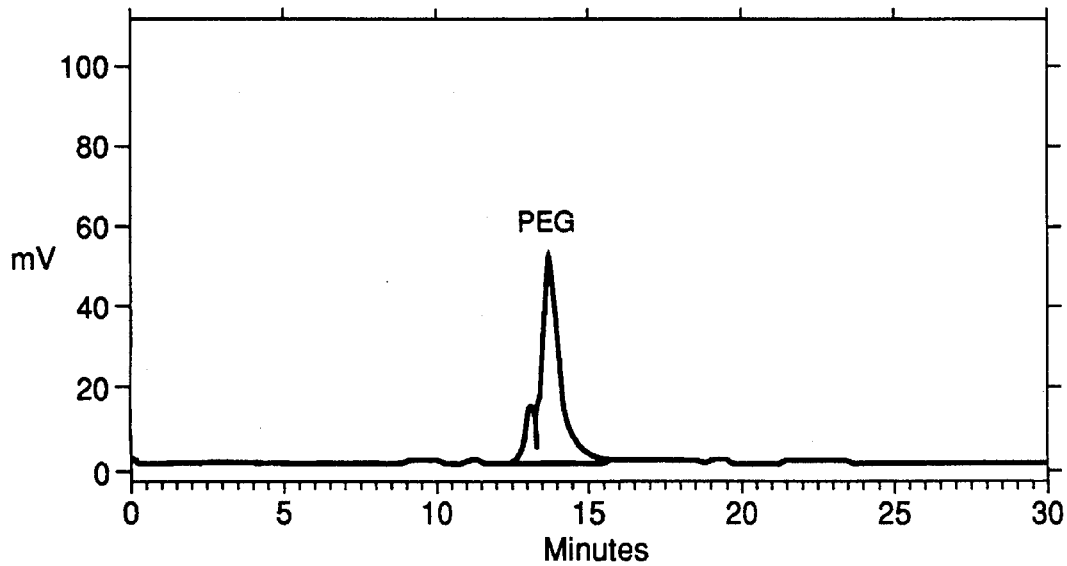
Figure 10C:
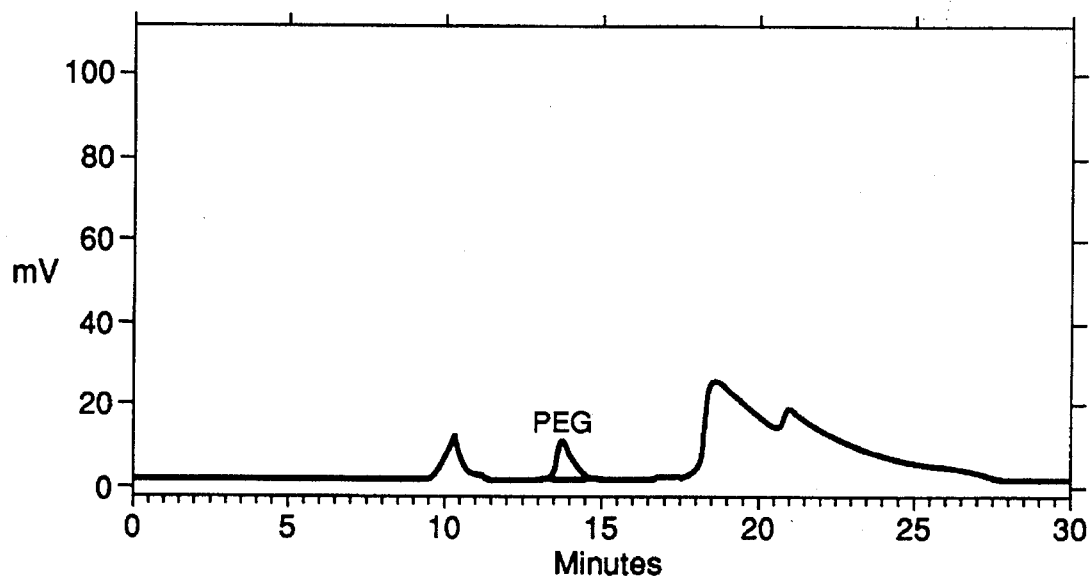
Figure 10D:
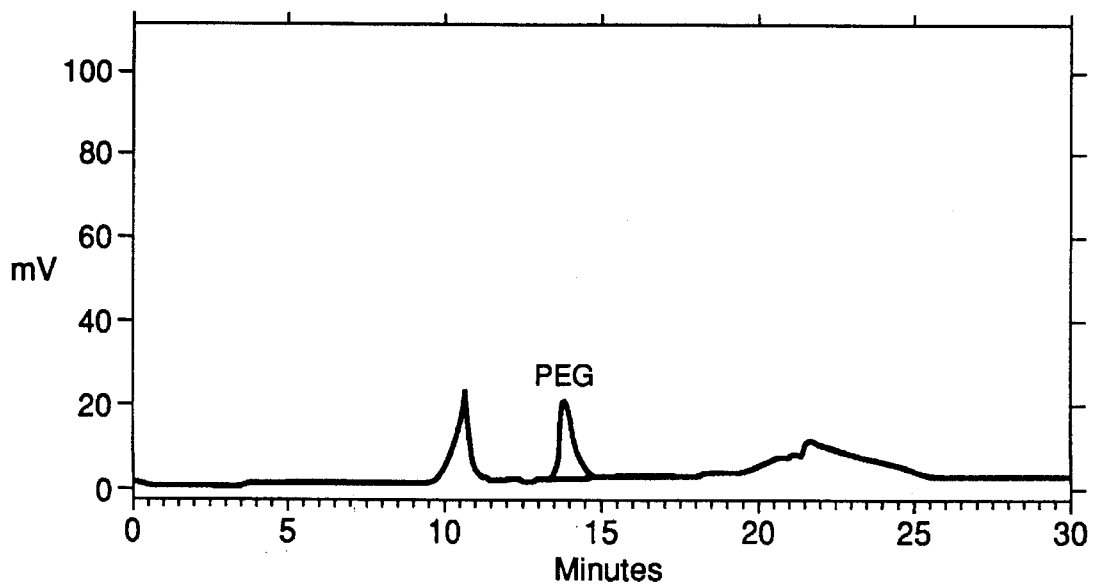

PEG Component: The elution profile of high diol HMW samples after base hydrolysis at pH 12.3 is shown in FIG. 10A. The SEHPLC chromatogram of high diol PEG-SS (5000 MW) is shown in FIG. 10B. Base hydrolysis of low diol HMW and LMW samples produce elution profiles as shown in FIGS. 10C and 10D, respectively. A composite table of retention times of PEG produced from base hydrolysis of different diol preparations of PEG-SOD, as well as reference compounds are shown in Table 2.

TABLE 2

PEG CHROMATOGRAPHY
PEG-SOD HMW Base Hydrolysis Products from High and
Low Diol Preparations and Different Molecular Weight PEGs
and Retention Times

| Sample | Diol(H/L) | Retention Time | Peak # | % |
|---|---|---|---|---|
| PEG-SOD, HMW | High | 13.19 | 1 | 24 |
|  | High | 13.72 | 2 | 76 |
| PEG-SOD, HMW | Low | 13.19 | 1 | 5 |
|  | Low | 13.72 | 2 | 95 |
| MeO-PEG 5000 | High | 13.05 | 1 | 28 |
|  | High | 13.59 | 2 | 72 |
| MeO-PEG 5000 | Low | 13.19 | 1 | 1 |
|  | Low | 13.72 | 2 | 99 |
| Peg 8000 | * | 13.14 | 1 | 100 |
| Peg 10000 | * | 12.82 | 1 | 100 |

*Used as molecular weight marker, being 100% diol.

Figure 9A:
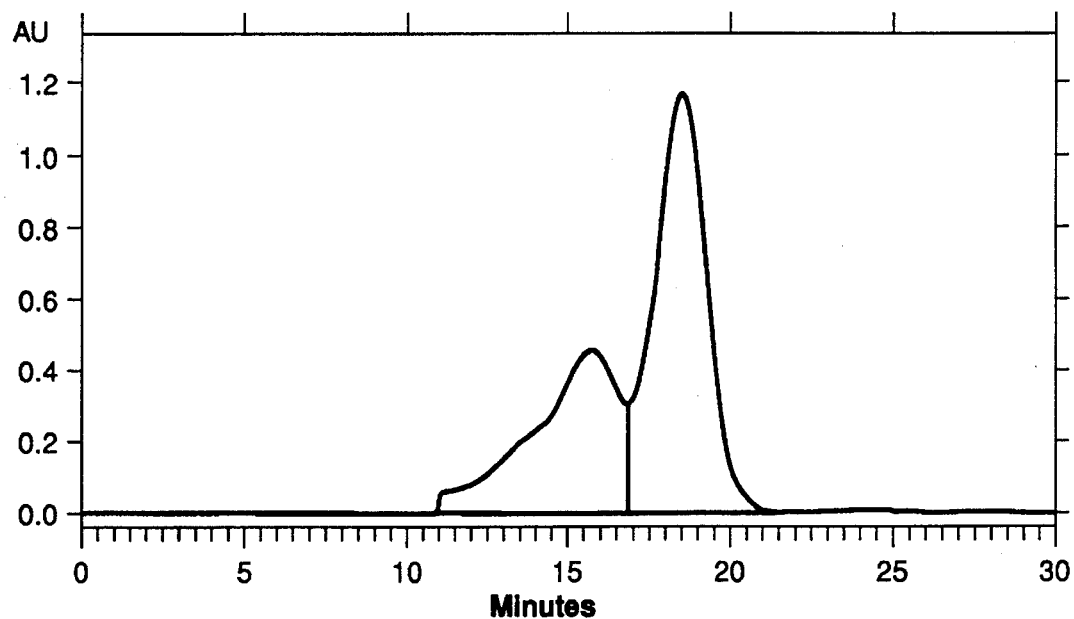
FIG. 9 represents profiles of high diol PEG-SOD subjected to base hydrolysis.
Figure 9B:
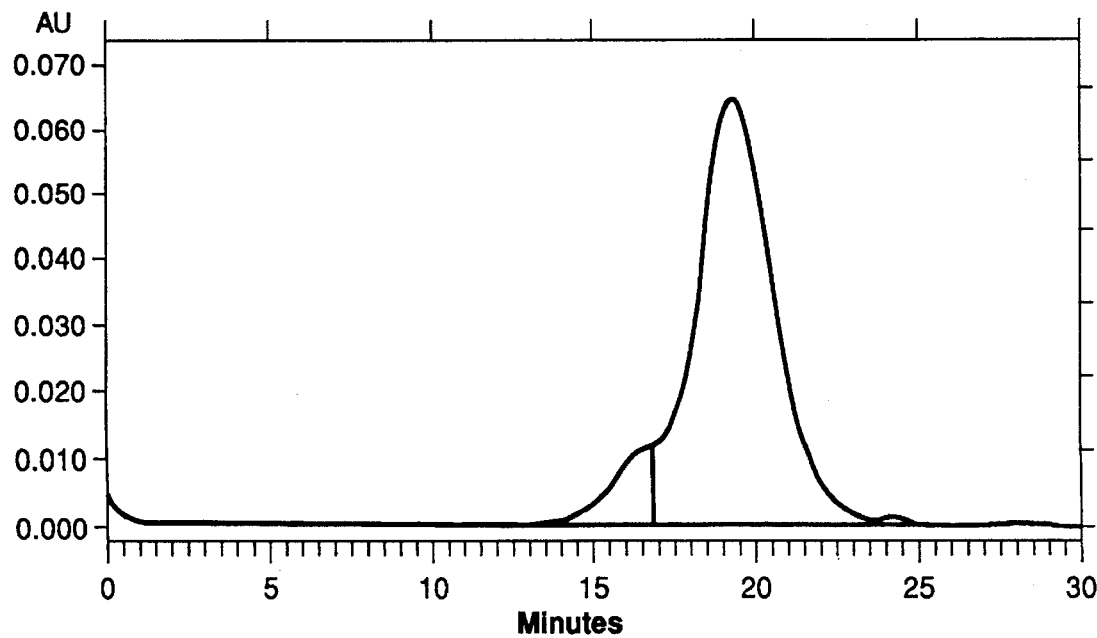
Figure 9C:
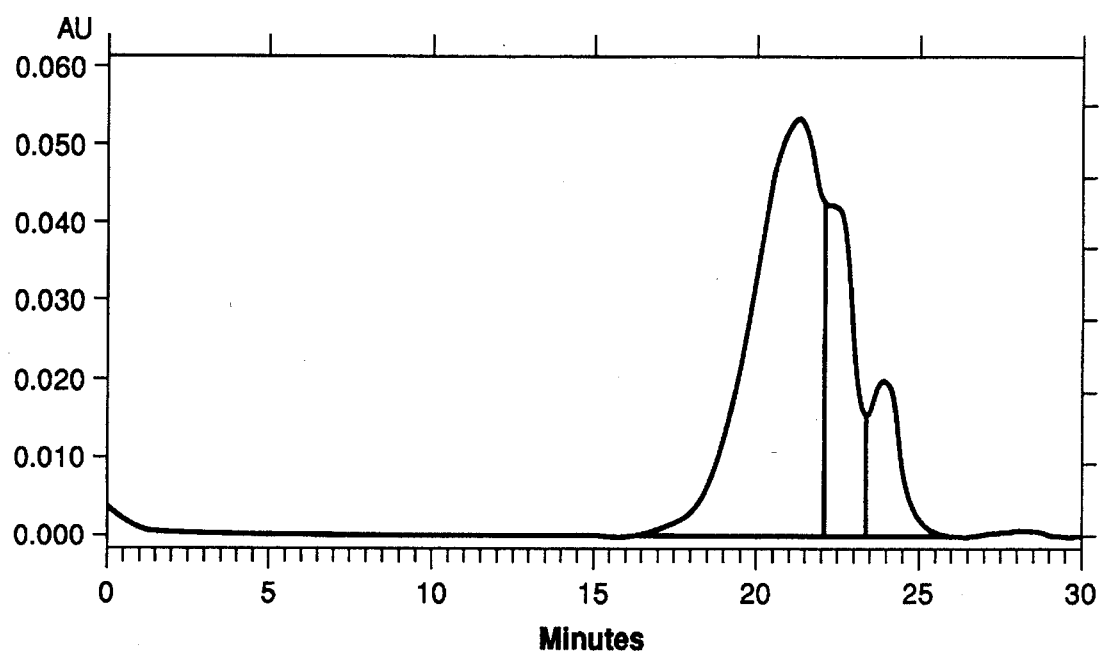
Figure 9D:
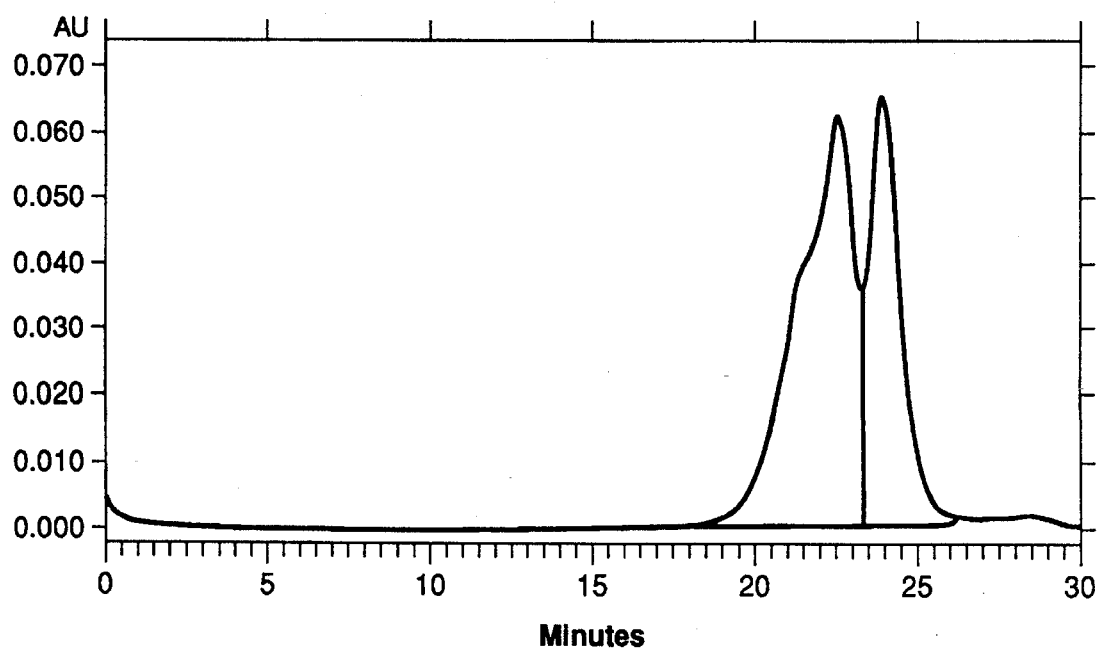
Figure 9E:
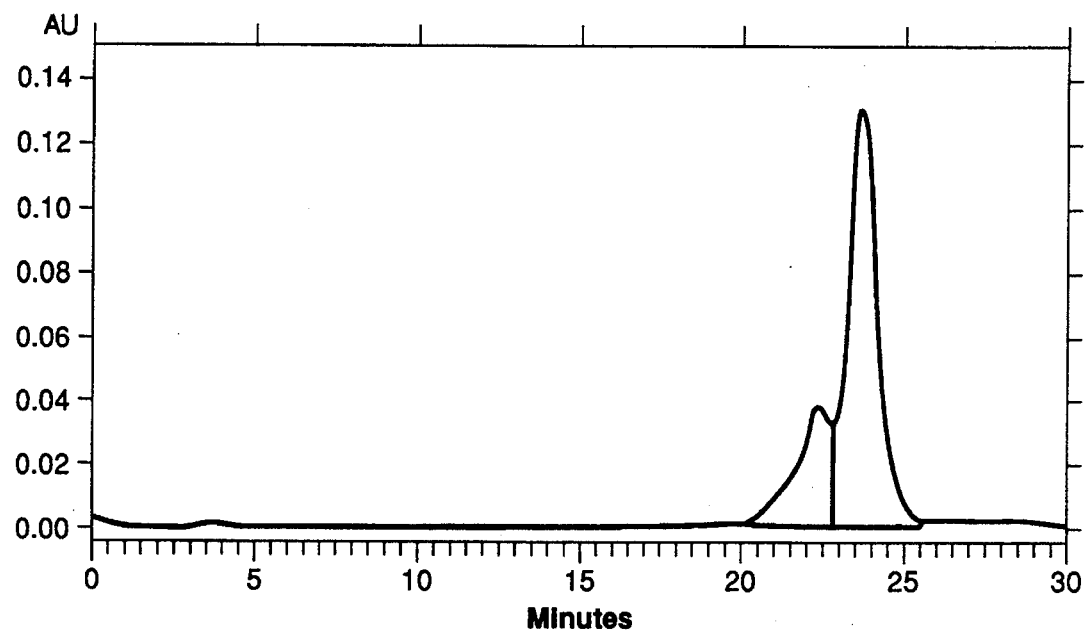
Figure 9F:
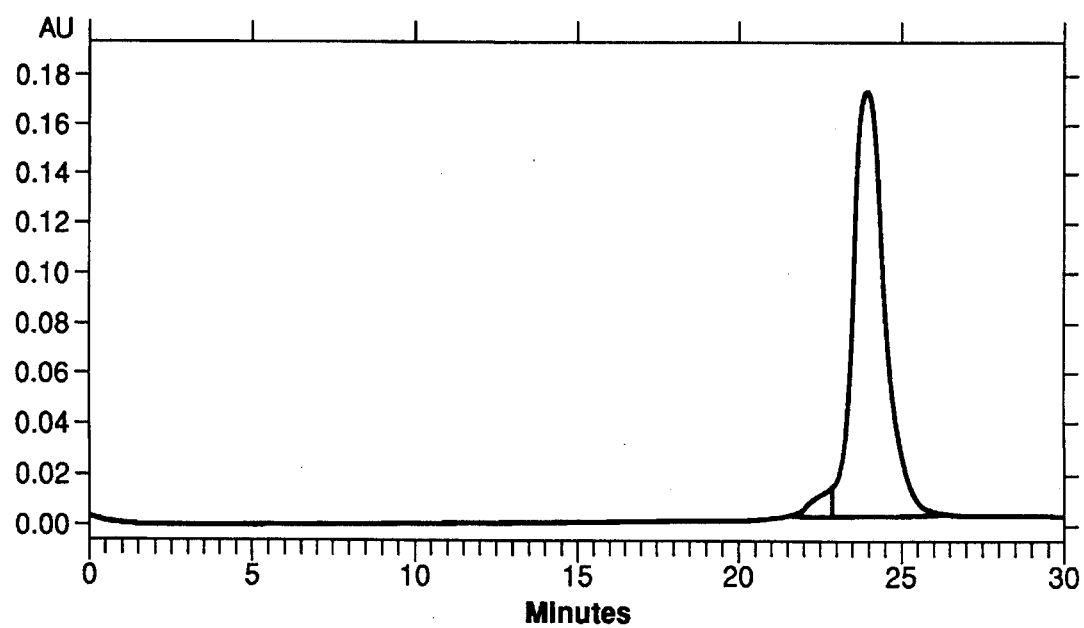
Figure 9G:
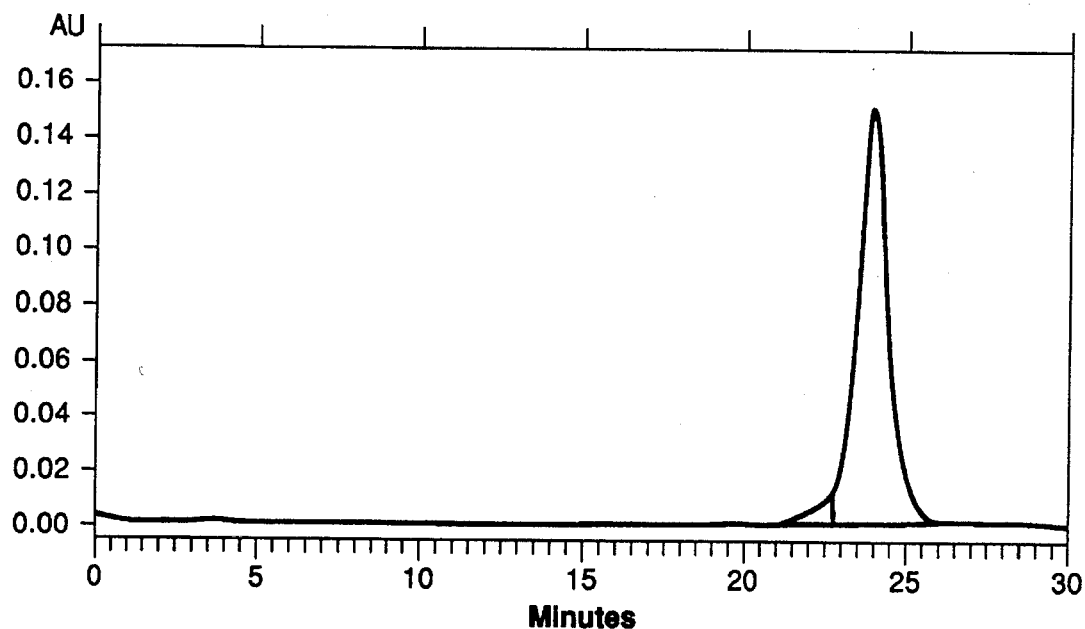
Figure 9H:
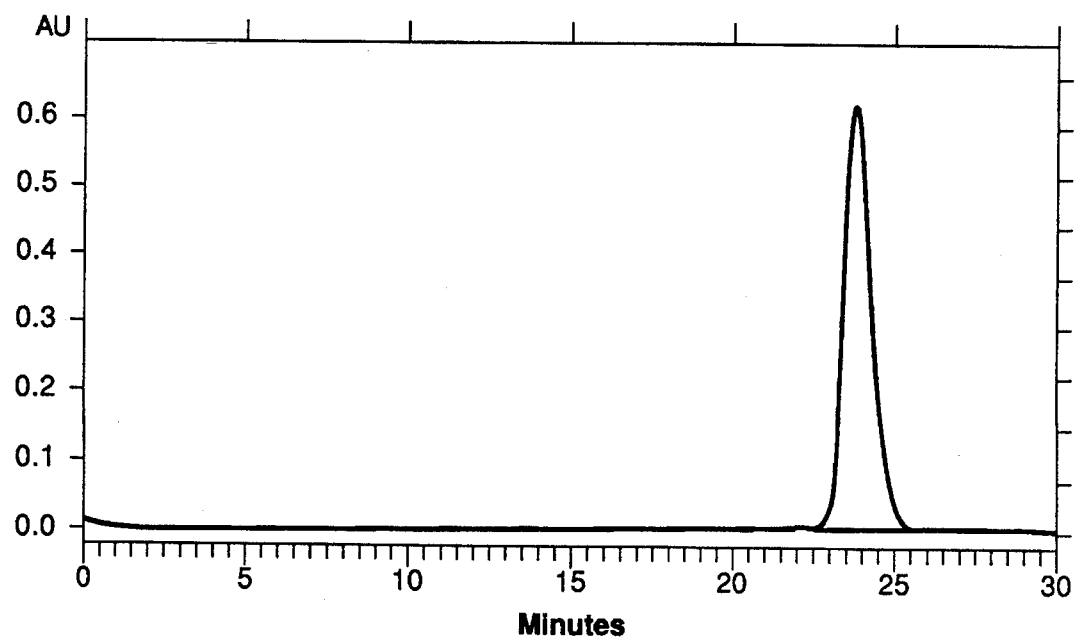
Figure 9I:
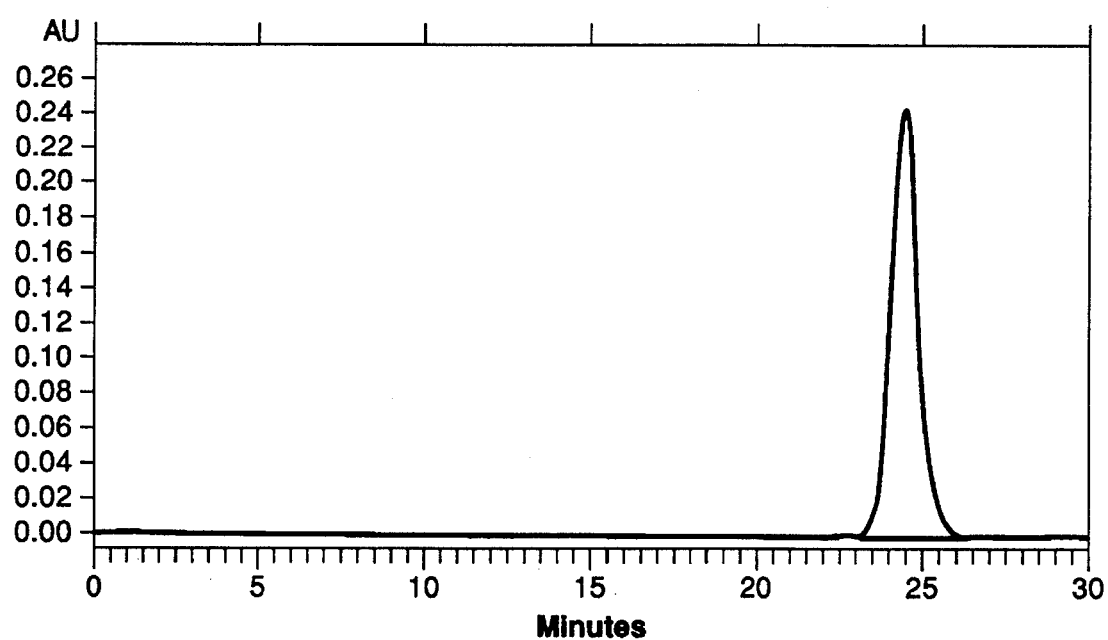

When high diol PEG-SOD is subjected to different degrees of base hydrolysis (FIG. 9), a peak that closely corresponds to succinyl-SOD (retention time: 23.8 minutes), begins to appear when the hydrolysis pH is adjusted to values >10.8 (FIG. 9C). As the pH increases from 10.8 to 12.3, there is a progressive loss of the original PEG-SOD peak, while a peak that resembles succinyl-SOD begins to appear. Finally, between pH 12.0 and 12.3 (FIGS. 9F and G), the hydrolysis seems to be complete and the end product has a retention time similar to that of succinyl-SOD. Even under mildly basic conditions (FIG. 9B), the HMW signal is extremely sensitive to base, indicating that a primary linkage comprising this species is probably an ester bond. These data are fundamental in characterizing the HMW material. Though not presented here, unfractionated PEG-SOD and HMW material exposed to sodium dodecyl sulfate (SDS treatment), remained intact indicating that HMW material is not held together by ionic bonds. Also, on reduction with mercaptoethanol in the presence of SDS the HMW material remained intact indicating that it is not held together by disulfide bonds.

When base hydrolysis is performed on the HMW material from both high and low diol PEG-SOD, the resulting hydrolysate from each preparation has significantly different elution profiles for free MeO-PEG (FIG. 10). As seen in FIG. 10A, the HMW from high diol PEG-SOD produces a PEG peak which is bimodal in nature, with peaks at 13.2 and 13.7 minutes, corresponding to molecular weights of 8000 and 5000, respectively (Table 2). The MeO-PEG used in the pegation reaction has an 'average' molecular weight of 5000. The presence of the 8000 MW PEG is related to diol material which arises during ethylene oxide polymerization and which leads to formation of a PEG polymer of higher molecular weight via chain growth at both ends of the polymer (i.e., to 8000 as compared to 5000). The ratio of the PEG 8000 to 5000 peak areas in hydrolyzed HMW was observed to be approximately 24:76 while the corresponding value for the PEG-SS starting material was 14:86. Therefore, it is apparent that there is a higher proportion of 8000 MW PEG in the HMW material. Conversely, when either HMW or LMW fractions from low diol PEG-SOD are analyzed after base hydrolysis, the prominent peak (i.e. >95%) corresponds to that of PEG 5000 MW with minor amounts of 8000 MW PEG (HMW–5% and LMW <1%; FIGS. 10C and D). The 8000 MW PEG contaminant is already present in the low diol PEG-SS (Table 2), and similar to the observations made with the high diol PEG-SOD, the 8000 MW PEG seems to accumulate in the HMW material. It is evident from these studies that the 8000 MW PEG SEHPLC signal can be used as a marker to determine (after base hydrolysis) the extent of crosslinked PEG-SOD in the preparation.

The study results indicate that the extent of HMW material formed in the final PEG-SOD product is related to the diol content of the MeO-PEG used in the synthesis. The SOD concentration used in the reaction mixture may also influence the extent of HMW material formed (by mass action) but the underlying mechanism for the formation of HMW appears to be due to crosslinking of SOD molecules mediated by bis-SS-PEG.

Starting Materials, Intermediates and Reagents

Superoxide Dismutase

Superoxide dismutase is the name given to a class of enzymes that catalyze the breakdown of the superoxide anion radical ($O_2-$.) to oxygen and hydrogen peroxide.

SOD is known under the systematic nomenclature of the International Union of Biochemistry as superoxide oxidoreductase and has a classification number of 1.15.1.1. Such substances have been called orgoteins and hemocupreins as well as superoxide dismutases and range in molecular weight from about 4,000 to about 48,000. The copper-zinc dismutases are a remarkably conserved family with respect to gross structural properties. Without exception, the purified enzymes have been shown to be dimers (molecular weight usually 31,000–33,000) containing two moles each of copper and zinc ions per mole. The enzymes of the manganese/iron family are not as uniform in such basic properties as molecular weight, subunit structure and metal content. Some are dimers; others are tetramers. The content of metal ranges from about 0.5 to 1 mole per mole of subunit polypeptide chain. Naturally occurring Zn/Cu-containing enzymes from mammals and their functionally competent analogs and muteins are considered to be mammalian Zn/Cu superoxide dismutases (mSOD).

In formulations of the present invention mSOD may be of any origin. It is commercially obtained from bovine erythrocytes and human erythrocytes as well as by recombinant synthesis in microorganisms, such as *E-coli* and yeast. Among other sources, Cupri-Zinc bovine liver superoxide dismutase (SOD, EC 1.15.1.1) for example, is available from DDI Pharmaceuticals, Inc. (Mountain View, Calif.).

Polyethylene Glycol

In practicing the present invention, low diol PEG is utilized for attachment to biologically active proteins. While certain molecular weight methoxypolyethylene glycols are available commercially (for example, methoxy-PEG$_{5,000}$ was obtained from Union Carbide Corporation in two forms: a conventionally available high diol methoxy-PEG$_{5,000}$ which contained 14–17% of higher molecular weight PEG diol, and a low diol product which contained less than 4% PEG diol) some are required to be made and purified in order to produce a pegated protein that possesses low immunogenicity. For example, pegation of SOD with methoxy-PEG-SS derived from some commercial sources leads to a product containing high molecular weight components, as verified by size exclusion chromatography, discussed earlier. This high molecular weight product is believed to derive from protein crosslinking through an activated diester formed from the various amounts of PEG diol found in the commercial sources of M-PEG. The individual active esters, although located on the same polymer chain, are nonetheless chemically remote from one another. Thus, the presence of a second reactive functionality in the polymer tends to exert an increasingly negligible effect on the reactivity of a first reactive functionality as the distance separating the two functionalities increases. The individual reactivities thus tend to be independent of moieties present at opposite ends of the polymer chain, and crosslinking cannot be avoided in the absence of infinite dilution of reagents. It is, accordingly, important to synthesize an M-PEG-SS known to contain very small amounts, preferably no amounts of diester. S. Zalipsky et al in the *Journal of Bioactive and Compatible Polymers*, Vol. 5, April 1990, pp. 227–231, described the purification of polyethylene glycol 2000 from methoxypolyethylene glycol 2000. The succinate esters are also prepared and shown to separate by ion exchange chromatography on DEAE-Sephadex. The preparative method is shown in Example 4.

While the procedure described in Example 4 works well with PEG-2000, it fails with higher molecular weight PEG's. Higher molecular weight PEG acids do not bind to anion or cation resins; the greater mass of polyethylene backbone is believed to mask any ionic properties of the pendant acid. We have found that extremely low ionic strength buffer was required to bind the PEG succinates and they eluted under very low increases of ionic strength indicating that they are only very weakly held by the resin.

We have found that higher molecular weight methoxy-PEGs can be separated from diol components if the hydroxyl functionalities are first converted to dimethoxytrityl (DMT) ethers before application of reverse phase thin layer chromatography. The hydroxyls can be liberated by acid treatment.

The schematics of preparation and purification of methoxy-PEG $_{5000}$-dimethoxytrityl (M-PEG-DMT) derivatives are as follows; while the details are shown in Examples 5 through 8.

M-PEG-DMT and DMT-PEG-DMT are prepared in an identical fashion. The polyether is dissolved in ethanol-free chloroform and the solution dried by distilling off approximately half the chloroform at atmospheric pressure under a blanket of argon. The solution is then allowed to cool to room temperature under argon, followed by the sequential addition of excess diisopropylethyl amine (1.5 eq.), 10 mol % 4-dimethylaminopyridine as catalyst, and finally an excess amount of 4,4-dimethoxytrityl chloride (1.2 eq.). After 15 hours reaction, the solution is concentrated by rotary evaporation and the solution added to anhydrous ether to precipitate the tritylated PEG. Regular phase TLC cleanly separates starting material from product, the PEG backbone staining with Dragendorfs reagent. While M-PEG-DMT is not resolved from DMT-PEG-DMT by regular phase TLC, reverse phase C-18 TLC plates cleanly separate M-PEG-DMT, DMT-PEG-DMT, DMT chloride and DMT alcohol from each other (mobile phase 4:1:1 acetonitrile/water/isopropanol). PEG backbone is confirmed by staining orange to Dragendorf's and trityl incorporation confirmed by exposing the plate to HCl vapors to give an orange stain.

Authentic M-PEG-DMT 5000 was shown to separate cleanly from authentic DMT-PEG-DMT 8000 on a Waters C-8, 300 angstrom pore size, 15–20 micron particle size Prep-Pak Bondapak cartridge. The crude M-PEG-DMT was dissolved by sonication in 30% acetonitrile/water to a concentration of approximately 12 mg/ml and passed through a 2.5 micron filter. The sample was loaded onto the column (2 g in 25 ml) in a 30% acetonitrile/water mobile phase. After 8 minutes of isocratic elution, a contaminating peak eluted (identity unknown, having a high absorbance at 280 nm but accounting for very low relative mass). A gradient of 30–70% acetonitrile/water over 21 minutes was then begun, and the desired M-PEG-DMT eluted at 58–60% acetonitrile. Authentic DMT-PEG-DMT typically elutes at 80% acetonitrile. The first ¾ of the desired peak is collected and the last ¼ discarded. In this way, 15.4 g of M-PEG-DMT was purified from 22.6 g of crude M-PEG-DMT.

The trityl cleavage of M-PEG-DMT is as follows:

Attempted removal of the DMT group from M-PEG-DMT with HCl gave by TLC (crude undiluted reaction mixture) complete removal of the trityl group. However, concentration of the chloroform extract gave a back reaction which resulted in a re-tritylation of a significant portion of the PEG. It was not possible to purify this by selective precipitation. The hydrated trityl cation and chloride are apparently in equilibrium with the result that dehydration, such as occurs during solvent removal, produces significant quantities of DMT chloride. This re-tritylation may be prevented by the use of a non-equilibrating counterion. Sulfuric acid was shown to irreversibly de-tritylate M-PEG-DMT. The sulfuric acid cleaved M-PEG is extracted into chloroform, concentrated and precipitated into ether to give pure zero diol M-PEG. In this manner, 10 g of M-PEG-DMT was cleaved to 8.68 g of zero diol M-PEG. Size exclusion chromatography indicates this material contains less than 0.3% diol.

Other higher molecular weight methoxy-PEG derivatives can be made by analogous processes.

The following examples will serve better to illustrate the practice of the present invention.

EXAMPLE 1

A. Methoxypolyethylene Glycol Succinate (M-PEG-S)

In a 2 liter flask, 100 g (0.02 mole) of methoxy-PEG$_{5,000}$ (M-PEG) was dissolved with stirring in 300 ml of warm (40° C.) anhydrous toluene. The volume was reduced by azeotropic removal of 147 ml of toluene under a nitrogen atmosphere to reduce the water content of the m-PEG from 1.73 to 0.23%. After cooling to ambient temperature, 233 ml of dry methylene chloride followed by 3.0 g (0.09 moles) of succinic anhydride and 1.1 g (0.01 mole) of 4-dimethylaminopyridine (DMAP) were added. The reaction was stirred and heated at reflux overnight, and then 200 ml of methylene chloride was removed at reduced pressure. The residue was added with stirring to 1.6 liters of ether in a 4 liter flask. This was stirred for 45 minutes and filtered. The filter cake was washed with 70 ml of ether and dried at reduced pressure to afford 100.4 g of crude m-PEG-succinate m-PEG-S) as a white solid containing DMAP.

The crude M-PEG-S (100 g) was dissolved in 633 ml of methylene chloride and passed through a column containing 114 g of Dowex 50x8–100H+ resin previously washed with 272 ml dioxane followed by 316 ml of dry methylene chloride. The column was then washed with an additional 316 ml of methylene chloride, and the eluents were combined and dried over anhydrous magnesium sulfate. Methylene chloride (800 ml) was removed under reduced pressure. The remaining solution was added with stirring to 1600 ml of ether in a 4000 ml flask. After stirring for 30 minutes, the suspension was allowed to stand for 30 minutes and then filtered. The filter cake was then washed with 75 ml of ether and dried at reduced pressure. This afforded 96.0 g (94% yield) of m-PEG-S as a white solid which exhibited a proton NMR spectrum consistent with the assigned structure: $^1$H-NMR (CDCl$_3$): 4.27 (triplet, 2H, —CH$_2$—O—C(=O)—), 3.68 (large singlet offscale, PEG methylene O—CH$_2$—'s), 3.39 (singlet, 3H, OCH$_3$), and 2.65 ppm (narrow multiplet, 4H, —C(=O)—CH$_2$—CH$_2$—C(=O)—). The carboxylic acid content of 0.000207 mol/g was measured by titration.

B. Methoxypolyethylene Glycol N-Succinimidyl Succinate (M-PEG-SS)

In a 2,000 ml flask, 98.48 g (0.0192 mole) of methoxypolyethylene glycol succinate (m-PEG-S) was dissolved in 468 ml of dry toluene with warming to 40° C. The solution was filtered and the volume was reduced by 263 ml by azeotropic distillation under nitrogen. The resultant viscous liquid was transferred to a 1,000 ml three-necked flask under nitrogen using 225 ml of dry methylene chloride. To this was added 2.22 g (0.0192 mole) of N-hydroxysuccinimide, and the reaction was stirred until the N-hydroxysuccinimide dissolved. The reaction mixture was then cooled to 5° C. in an ice bath, and a solution of 4.44 g (0.0125 mole) of dicyclohexylcarbodiimide (DCC) in 24 ml of methylene chloride was added dropwise over 5 minutes. During the addition of the methylene chloride/DCC solution, dicyclohexylurea (DCU) began to crystallize from the reaction mixture. The reaction was allowed to warm to room temperature and was stirred overnight. The content of the reaction flask was transferred to a 2,000 ml flask using 25 ml of methylene chloride to rinse the flask. At reduced pressure at 30° C., 250 ml of methylene chloride was removed, the suspension was filtered and the filter cake was washed with 25 ml of dry toluene. The filtrate was then added to 1,200 ml of anhydrous ether with stirring, and the resultant suspension was stirred for 45 minutes before being filtered. The filter cake was rinsed with 100 ml of dry ether and dried under a latex rubber dam for 2 hours. The resultant solid was then dried under high vacuum and transferred to a bottle in a glove bag under argon. This afforded 96.13 g (96.1% yield) of the title compound (m-PEG-SS) as a white solid which exhibited a proton NMR spectrum consistent with the assigned structure: $^1$H-NMR (CDCl$_3$): 4.32 (triplet, 2H, —CH$_2$—O—C(=O)—), 3.68 (large singlet offscale, PEG methylene O—CH$_2$—'s), 3.39 (singlet, 3H, OCH$_3$), 2.99 and 2.80 (pair of triplets, each 2H, succinate —C(=O)—CH$_2$CH$_2$—C(=O)—), and 2.85 ppm (singlet, 4H, succinimide —C(=O)—CH$_2$CH$_2$—C(=O)—). The active ester content of the product was determined by reaction with excess benzylamine in toluene followed by back titration with perchloric acid in dioxane to a methyl red end-point and found to be 0.000182 mole/g.

C. Low Diol PEG-SOD 11.8 g of an aqueous solution of SOD containing 82.1 mg of protein per gram was diluted to a total weight of 200 g with 0.1M sodium phosphate buffer at pH 7.8. To this solution, magnetically stirred and heated to 30° C., was added 3.4 g of low diol methoxy PEG-SS prepared in Example 1B. The pH of the reaction mixture was maintained at 7.8 using a Merrier DL25 titrator programmed in the pH star mode to add 0.5 normal sodium hydroxide solution as required. After 1 hour the reaction mixture was filtered through a 0.2 micron low protein binding polysulfone filter, concentrated to about 60 ml using a stainless steel Millipore Mini-tan device equipped with a 30,000 NMWL membrane 4 pk and was then subjected to dialfiltration against 2 liters of 50 mM sodium phosphate buffered saline (0.85%) at pH 6.2 to 6.3. The retentate solution containing the low diol PEG-SOD was then filtered through a 0.2 micron filter.

EXAMPLE 2

High Diol PEG-SOD

A high diol PEG-SOD was prepared in the same manner as low diol PEG-SOD using high diol PEG-SS.

EXAMPLE 3

A. Monomethoxypolyethylene glycol succinate

A 12 liter three-neck flask was charged with 4 liters of toluene and 2212 g of methoxypolyethylene glycol, previously warmed to 70° C. under nitrogen. The volume was reduced by azeotropically removing 1.3 liters of toluene at reduced pressure. After cooling to 30° C., there was added 4 liters of methylene chloride followed by 66.4 g of succinic anhydride and 24.4 g of 4-dimethylaminopyridine. The reaction was refluxed for 32 hours then 3.8 liters of methylene chloride was removed at atmospheric pressure. The reaction was cooled and poured into a 5 gal. glass carboy containing 28 liters of methyl tert-butyl ether with stirring. The resulting suspension was stirred for 1 hour and collected on a Lapp filter. The filter cake was washed with 1 liter of methyl tert-butyl ether. Drying in a vacuum over overnight at room temperature yielded 2.252 kg of the title compound as a crude white solid.

The crude title compound was dissolved in 8 liters of methylene chloride and passed through a glass pressure column containing 3.0 kg of Dowex 50W-X8 resin (cation exchange, hydrogen form) previously washed with 5 liters acetone followed by 4 liters of methylene chloride. The column was then washed with 3 liters of methylene chloride. The column eluents were combined and 10 liters of methylene chloride was removed at atmospheric pressure. The remaining solution was poured into 26 liters of methyl tert-butyl ether with stirring. The resulting suspension was stirred for 45 minutes and the solid was removed by filtration. This was washed with 3 liters of methyl tert-butyl ether. Drying in a vacuum oven at room temperature yielded 2.46 kg of a white solid of the title compound, 95% recovery. This material contained 1.5% methoxypolyethylene glycol, and assayed at $2.72 \times 10^{-4}$ mole/g (theory is $1.96 \times 10^{-4}$ mole/g).

B. Methoxypolyethylene glycol N-succinimidyl succinate

In a 12 liter flask under nitrogen 1.5 kg of monomethoxypoly ethylene glycol succinate was dissolved in 7.2 liters of toluene with warming. The volume was reduced by 2.8 liters at reduced pressure to remove water. The resultant viscous liquid was cooled to 40°–45° C. and 3.4 liters of methylene chloride was added followed by 33.89 g of N-hydroxysuccinimide. The reaction was stirred for 1 hour until all the N-hydroxysuccinimide was dissolved, then the reaction was cooled to 10° C. and a methylene chloride solution (368 ml) of 67.75 g 1,3-dicyclohexylcarbodiimide (DCC) was added dropwise over 30 minutes. The reaction was allowed to warm slowly to room temperature while being stirred over 18 hours. The volume was then reduced by 3.2 liters at atmospheric pressure. The suspension was cooled to 0°–5° C. and stirred for 30 minutes. This was filtered and the filter cake was washed with 250 ml of toluene. The filtrate and the wash was added to 28 liters of methyl tert-butyl ether with stirring. The resultant suspension was stirred for 45 minutes and then filtered on a Lapp filter. The filter cake was washed with 1 liter of methyl tert-butyl ether and dried under a latex dam for 4 hours. Additional drying at room temperature in a vacuum oven at reduced pressure overnight yielded 1.5 kg of a white solid, 100% yield. This material assayed at $1.79 \times 10^{-4}$ mole/g (theory is $1.92 \times 10^{-4}$ mole/g).

C. Methoxypolyethylene glycol succinoyl bovine superoxide dismutase

To 32 liters of warm (29°–30° C.) pH 7.8 phosphate buffer in a 42 liters reactor containing a pH electrode was added 194.0 g of bovine erythrocyte superoxide dismutase. The volume was adjusted to 39.5 liters and the reaction was warmed to 29° C. The sodium hydroxide tube from the pH titrator was adjusted over the center of the reactor directly above the surface of the solution. The pH titrator was initiated and the pH was adjusted to 7.8 with 0.5N sodium hydroxide. At this time 614.7 g of methoxypolyethylene glycol N-succinimidyl succinate was added over two minutes and the reaction was stirred for 41 minutes while the pH was being adjusted to 7.8 with 0.5N sodium hydroxide with the reaction temperature being maintained at 30° C. The reaction was then filtered through a 200 Millipak filter and concentrated using a Millipore stainless steel Pellicon diafiltration system. The reactor was then rinsed with 600 ml of pH 6.2 phosphate buffer. The rinse was added to the concentrate after filtering through the Millipore 200 filter and the dialfiltration system. The final volume of the concentrate was about 9 liters. The concentrate was then diafiltered, using the Millipore Pellicon diafiltration system against 200 liters of pH 6.2 phosphate buffer over 2.17 hours. The diafiltration system was rinsed with 1.5 liters of pH 6.2 phosphate buffer. The final volume of the concentrate was about 8 liters. The concentrate was then transferred to a clean 5 gal glass carboy through an inline Millipore 200 Millipak filter and the filter was rinsed with 500 ml of pH 6.2 phosphate buffer. This afforded 11.98 kg (91.4% yield) of the title compound as a clear greenish-blue solution. (Activity: 32,960 units/ml).

EXAMPLE 4

A. Preparation of partially carboxymethylated polyethylene oxide

Polyethylene oxide, $M_w$ 2000 (Fluka, 25 g, 25 meq. OH) was dissolved in toluene (120 ml) and azeotropically dried until no more water appeared in the Dean-Stark trap attachment (approx. 25 ml of toluene were removed). The solution was cooled to 50° C. and treated with potassium tert-butoxide (1.7 g, 15 mmol). The solution was brought to reflux and more solvent was distilled off (approx. 25 ml). The stirred reaction mixture was brought to 25° C., and treated overnight with ethyl bromoacetate (3.4 ml, 16 mmol). The precipitated salts were removed by gravity filtration, and washed with methylene chloride (30 ml). The polymer was recovered by partially concentrating the filtrate (to approx. 60 ml), and slowly pouring the concentrated solution into ethyl ether (300 ml) at 5° C. with vigorous stirring. The collected white polymeric powder was dried in vacuo. Yield: 24 g; IR (neat) showed the characteristic ester absorption at 1753 cm$^{-1}$. The polymer was dissolved in 1N NaOH (50 ml), and NaCl (10 g) was added. After approx. 45 min this solution was acidified with 6N HCl to pH 3.0 and extracted with methylene chloride (3×60 ml). The combined organic phases were dried (MgSO$_4$), concentrated (to approx. 50 ml), and poured into cold stirring ether (300 ml). The precipitated product was collected by filtration and dried in vacuo. Yield: 22 g; IR (neat) showed absorption at 1730 cm$^{-1}$, corresponding to ω-carboxyl group.

B. Preparation of pure
α-hydroxy-ω-carboxymethylpolyethylene oxide by separation of partially carboxymethylated PEO on DEAE-Sephadex The mixture of homo- and heterobifunctional PEO's (22 g) was dissolved in water (40 ml), and applied to a column containing DEAE-Sephadex A-25 (Sigma, 27 g, 0.1 mole ion-exchange sites) in the tetraborate form. The first fraction containing underivatized polymer was eluted with deionized water. When the eluent became negative to a PAA test, a stepwise ionic gradient of ammonium bicarbonate (from 6 to 22 mM at increments of 1–2 mM every 100 ml) was applied, and fraction collection (approx. 40 ml each) began. Fractions 2–21 were positive to the PAA test, and contained pure monocarboxylated PEO ($R_1$=0.49). The subsequent three fractions did not contain PEO, while fractions 25–36 contained the pure PEO-diacid ($R_1$=0.26). The fractions containing α-hydroxy-ω-carboxymethylpolyethylene oxide were combined and concentrated (to approx. 100 ml). Sodium chloride (35 g) was dissolved in this solution, which was then acidified to pH 3 and extracted with methylene chloride (3×100 ml). The combined CH$_2$Cl$_2$ solution was dried (MgSO$_4$), concentrated (to approx. 100 ml), and slowly poured into cold stirring ether (500 ml). The precipitated polymer was collected and thoroughly dried in vacuo to give 8.8 g of product. $^{13}$C-NMR (CDCl$_3$): δ172.7 (COOH); 72.4 (CH$_2$CH$_2$OH); 70.4 (PEO); 69.0 (CH$_2$COOH); 61.3 (CH$_2$OH)ppm.

Bis-carboxymethylpolyethylene oxide isolated from the column was also analyzed. $^{13}$C-NMR (CDCl$_3$): δ172.4 (COOH); 70.4 (PEO); 68.8 (CH$_2$COOH) ppm.

EXAMPLE 5

Synthesis of dimethoxytrityl methoxypolyethylene glycol

Methoxypolyethylene glycol (5,000 dalton average molecular weight; 36.3 g, 7.26 mmol) was dissolved in 500 ml chloroform, followed by the removal by distillation of 250 ml chloroform to remove water. A drying tube was attached to the flask and the solution allowed to cool to approximately 50° C. N,N-diisopropylethylamine (1.8 ml, 10.3 mmol) was added, followed by 4-dimethylamino pyridine (100 mg, 0.8 mmol, 10 mol %) and 2.9 g of 4,4-dimethoxytrityl chloride (98%).

The mix was allowed to stir overnight at room temperature at which time the solvent was removed by rotary evaporation at 60° C. The residue was taken up in a small amount of chloroform, and the M-PEG-DMT was precipitated by addition into 2 liters of anhydrous ether. The precipatate was collected, dried and chromatographed on a C-8 300A reverse phase prep column on a Waters LC4000 system employing a 30–95% acetonitrile gradient (against water) over 20 minutes. The desired product eluted at 58–60% acetonitrile. The sample (2 g) in 20 ml of 30% acetonitrile/water was loaded onto the column at 50 ml/min flow rate. This eluent (30% acetonitrile/water) was allowed to continue isocratically until a large impurity peak was eluted, typically 3–5 min, mv 280 μm. After the elution of this first peak, the gradient was started. The next peak to elute was the desired methoxy-PEG-DMT 5000. The first ¾ of the peak was collected, and the tail end of the peak was discarded.

In this fashion, 22.6 g of crude M-PEG-DMT 5000 was purified in 2 g portions to obtain 15.44 g of the title product.

EXAMPLE 6

Synthesis of zero diol methoxypolyethylene glycol from dimethoxytrityl methoxypolyethylene glycol 10 g M-PEG-DMT 5000 was placed in a 500 ml flask and dissolved in 320 ml Milli-Q water. Sulfuric acid was added (80 ml) as a slow stream to bring the concentration to 20%. The solution turned red and homogeneous. After stirring overnight, the acid solution was extracted with 2×500 ml chloroform, and the combined extracts dried over MgSO$_4$, concentrated, and the red oil poured as a thin stream into 2 liters of anhydrous ether at 20° C. The precipitate was allowed to settle for 24 hours. It was collected in a course frit sintered glass funnel, and then washed with 2×200 ml portions of anhydrous ether. The precipitate cake was broken up and dried under vacuum to yield 8.68 g methoxy-PEG 5000 (zero diol).

EXAMPLE 7

Synthesis of zero diol methoxypolyethylene glycol succinate from zero diol methoxypolyethylene glycol M-PEG-OH 5000 zero diol (4.7 g, 0.94 mmol) was dissolved in 100 ml toluene. The solution was brought to reflux and a Dean-Stark trap was used to remove any water. After 1 hour at reflux, a total of 80 ml toluene was removed by distillation, and the vessel containing 20 ml toluene, was allowed to cool under argon positive pressure. Succinic anhydride was added (110 mg, 1.1 mmol), followed by 4-dimethylaminopyridine (137 mg, 1.12 mmol). Since the succinic anhydride did not dissolve, 10 ml of anhydrous ethanol free chloroform was added, and the solution was held at a reflux using an oven dried condenser. After 15 h at reflux, the solution was cooled and then stirred with 10 g of cation exchange resin, filtered, and the filtrate concentrated to obtain the title compound.

EXAMPLE 8

Synthesis of zero diol methoxypolyethylene glycol succinimidyl succinate from zero diol methoxypolyethylene glycol succinate A solution of M-PEG-succinate from Example 7 (4.15 g, 0.83 mmol) in 100 ml of toluene was dried azeotropically. A portion of the toluene was distilled off (60 ml, leaving 40 ml in the reaction flask) and N-hydroxysuccinimide (100 mg, 0.87 mmol) was added, followed by the careful addition of 30 ml of ethanol free anhydrous chloroform. An additional 25 ml of the mixed solvent was removed by distillation and the solution was allowed to cool at room temperature under argon. DCC was added (200 mg, 9.7 mmol) and the solution was stirred. After 10 minutes, DCU began to crystallize out. After stirring for two days, an additional 25 mg (0.22 mmol) of N-hydroxy succinimide was added. The dicyclohexyl urea (DCU) slurry was filtered and the precipitate was washed with toluene. The filtrate was concentrated by rotary evaporation giving an additional precipitation of dicyclohexyl urea (DCU). The filtered concentrate was added dropwise into one liter of anhydrous ether. The precipitate was collected on a Whatman 9 cm 6F/F glass fiber filter and then dried under high vacuum for 15 hours, to give 3.37 g of M-PEG-SS.

Active ester content: $1.71 \times 10^{-4}$ mol/g; HPLC indicated: 1.3% M-PEG-S; other impurities: 1.2%; DCU none detected; total impurity: 3%.

EXAMPLE 9

Synthesis of zero diol PEG-SOD

Superoxide dismutase (1.33 ml of 75 mg/ml stock) was added to 18.67 ml of reaction buffer (100 mM sodium phosphate, pH 7.8) and the solution was brought to 30° C. M-PEG-SS from Example 8 (300 mg) was added in one portion and the pH was maintained at 7.8 by use of a pH stat. After 28 minutes the reaction pH became unchanging and the sample was concentrated on Centrium centrifugal membrane of 10,000 MW cutoff. The concentrated sample was exchanged in this manner with Dulbecco's PBS which had been adjusted to pH 6.2 with 1M HCl. Five exchanges at a total of 60 ml were performed. Size exclusion HPLC showed negligable high MW peak indicating that the title compound contained negligable amounts of material derived from diol (i.e., it was "zero diol").

The following examples illustrate the preparation of other biologically active proteins covalently joined to PEG.

EXAMPLE 10

Synthesis of low diol methoxypolyethylene glycol-succinoyl-catalase 4.17 ml of an aqueous suspension of catalase containing 24.0 mg of protein per ml was diluted with 15.84 ml of 0.1M sodium phosphate buffer, pH 7.8. To this solution, magnetically stirred and heated to 30° C., was added 550 mg of low diol methoxy PEG-SS. The pH of the reaction mixture was maintained at 7.8 using a Mettler DL25 titrator programmed in the pH stat mode to add 0.5 normal sodium hydroxide solution as required. After 0.5 hour the reaction mixture was filtered through a 0.45 micron low protein binding polysulfone filter and placed in two Amicon Centriprep 30 Concentrators (30K NMWL membrane) and buffer was exchanged several times with Dulbecco's PBS. The retentate solution containing the low diol PEG-catalase was then filtered through a 0.2 micron filter. Conjugate formation was demonstrated by SEHPLC and gel electrophoresis.

EXAMPLE 11

Synthesis of low diol PEG-Ovalbumin 503 mg of ovalbumin (Sigma) was dissolved in 50 g of 0.25M, pH 7.8 phosphate buffer at room temperature in a polyethylene beaker containing a Telfon-coated magnetic stir bar. After stirring for 15 minutes, 1.900 g of low diol M-PEG(5,000)-SS was added all at once. The pH of the reaction mixture was controlled at 7.8 with a Mettler DL25 pH stat which added 0.5N NaOH as needed. The reaction was allowed to continue for 1 h at room temperature, and then the reaction mixture was diafiltered through an Amicon YM30 membrane using a stirred cell device operated under 25 psi of argon overnight in a refrigerator at 4° C. After 800 ml of buffer had beed diafiltered, the product was concentrated by ultrafiltration, filtered through a 0.2 micron polysulfone filter, and vialed in sterile glass vials to give 44.3 g of solution with a protein content of 10.5 mg/ml. The degree of protein modification was determined to be 71.4 % by titration analysis of lysine amines.

EXAMPLE 12

Synthesis of low diol mPEG$_{5K}$-S-Ovalbumin 10 ml of a cold 10 mg/ml solution of ovalbumin (Sigma, grade VI) in 0.25M phosphate buffer, pH 7.4 was added to 382 mg of low diol mPEG$_{5K}$-SS and stirred at 5° C. for 16 hours. The product was purified in a Centriprep 30 Concentrator (Amicon, 30K NMWL membrane) using Dulbelco's PBS as the exchange buffer. The purified solution was filtered through a 0.2 μm filter to give 6.539 g containing 13.8 mg/ml of 74% modified (TNBS titration method) protein.

In a similar manner, 100 mg of ovalbumin was reacted with 283 mg of low diol mPEG$_{5K}$-SS giving 6.274 g containing 13.8 mg/ml of 74% modified protein.

In a similar manner, 100 mg of ovalbumin was reacted with 190 mg of low diol mPEG5K-SS giving 5.704 g containing 16.8 mg/ml of 67% modified protein.

EXAMPLE 13

Synthesis of low diol mPEG$_{5K}$-S-rhu-IL4

190 μl of a 5.26 mg/ml solution of rhu-IL4 (Immunex) was diluted with 772 μl of 0.1M borate buffer, pH 8.5. The rhu-IL4 solution was then treated with 29.2 μl of a 34 mg/ml solution of low diol methoxy PEG-SS in DMF. After 1 hour and 20 minutes at room temperature the reaction mixture was centrifuged and injected directly onto a preparative SEHPLC column. The purified conjugate was shown to be essentially a single band on gel electrophoresis.

EXAMPLE 14

Synthesis of low diol mPEG$_{5K}$-S-NT

A solution containing 8.7 mg of neurotensin (NT) (BaChem) in 2.175 ml of 0.25M phosphate buffer, pH 7.8 was added to 174 mg of low diol mPEGsK-SS. The reaction mixture was kept at room temperature for 1.75 hours, then refrigerated. Pure mono-mPEG$_{5K}$-S-NT was obtained after separation from NT-PEG$_{8K}$-NT by preparative reverse phase HPLC on a C-8 column eluting with a water/acetonitrile gradient.

Reactivity of Antibodies in Serum Treated with PEG-SOD

Enzyme-linked immunosorbent assays (ELISA) which detect circulating IgG antibodies to PEG-SOD were used to assess the immunoreactivity of low diol PEG-SOD and high diol PEG-SOD.

Subjects enrolled in Phase I clinical studies received intravenous injections of high diol PEG-SOD to produce antibodies in their serum. Serum was then collected from patients. A statistical analysis of the reactivity of circulating antibodies obtained from the Phase I study to preparations of low and high diol PEG-SOD both prepared with the same percent modification of lysine amines was investigated. This analysis examined the optical density differences among preparations across all subjects treated with high diol PEG-SOD. The optical densities (OD) of the post-treatment serum samples for low diol PEG-SOD were two to ten times less than those for the high diol PEG-SOD. This unexpected result implies that antibodies present in the post-treatment serum samples have little reactivity to low diol PEG-SOD, and that the immunogenicity of low diol PEG-SOD is considerably less than that of high diol PEG-SOD.

The method used in the analysis is as follows:

100 ml of 2.5 µg/ml solution of high and low diol PEG-SOD was added to wells of a CoBind microtiter plate. The plate was covered with Parafilm and incubated overnight at room temperature in the dark. Unbound PEG-SOD was removed from the wells of the microtiter plate by washing and aspirating five times with distilled water followed by thorough blotting. 200 µl of 1% gelatin in PBS was added to each well and incubated for approximately 1 hour at 37° C. The plates were then washed again five times with PBS containing 0.05% Tween 20 and thoroughly blotted. 100 µl of each diluted clinical sample was added in triplicate to the wells of the microtiter plate and incubated for one hour at room temperature. For each subject, a pre-dose sample and a post-dose sample was analyzed. Plates were washed again as described above. 100 µl of diluted goat anti-human immunoglobulin conjugated to horseradish peroxidase was added to each well and incubated for 1 hour at room temperature. Plates were again washed as described above. 100 µl of ABTS substrate solution was added to each of the wells and incubated for approximately 20 minutes at room temperature. Optical density readings for the individual wells were taken using a dual wavelength setting (405 nm read, 490 nm reference) on a BioTek EL 312 microplate reader. The magnitude of color development was directly related to the amount of antibody present in the sample. The results of the study are shown in Table 3.

TABLE 3

Relative Reactivity of ELISA-Positive Human Serum Samples with Low Diol PEG-SOD and High Diol PEG-SOD Preparations

| Subject ID | Sample | Mean OD Values[a] | |
|---|---|---|---|
| | | High Diol | Low Diol |
| 101 | 1[b] | 0.039 | 0.045 |
| | 2[c] | 0.135 | 0.139 |
| 102 | 1[b] | 0.061 | 0.072 |
| | 2[c] | 0.605 | 0.119 |
| 103 | 1[b] | 0.043 | 0.038 |
| | 2[c] | 0.707 | 0.393 |
| 104 | 1[b] | 0.092 | 0.119 |
| | 2[c] | 0.411 | 0.254 |
| 105 | 1[b] | 0.037 | 0.051 |
| | 2[c] | 0.331 | 0.114 |
| 106 | 1[b] | 0.316 | 0.235 |
| | 2[c] | 0.595 | 0.242 |
| 107 | 1[b] | 0.360 | 0.132 |
| | 2[c] | 0.896 | 0.771 |
| 108 | 1[b] | 0.123 | 0.103 |
| | 2[c] | 0.354 | 0.281 |
| 109 | 1[b] | 0.082 | 0.073 |
| | 2[c] | 0.214 | 0.113 |
| 110 | 1[b] | 0.296 | 0.075 |
| | 2[c] | 0.728 | 0.089 |
| 111 | 1[b] | 0.066 | 0.055 |
| | 2[c] | 0.355 | 0.119 |
| 112 | 1[b] | 0.064 | 0.208 |
| | 2[c] | 0.570 | 0.388 |
| 113 | 1[b] | 0.134 | 0.073 |
| | 2[c] | 0.384 | 0.086 |
| 114 | 1[b] | 0.049 | 0.048 |
| | 2[c] | 0.302 | 0.057 |
| 115 | 1[b] | 0.077 | 0.081 |
| | 2[c] | 0.678 | 0.307 |
| 116 | 1[b] | 0.079 | 0.071 |
| | 2[c] | 0.675 | 0.213 |
| 117 | 1[b] | 0.077 | 0.087 |
| | 2[c] | 0.335 | 0.161 |
| 118 | 1[b] | 0.209 | 0.121 |
| | 2[c] | 0.531 | 0.152 |
| 119 | 1[b] | 0.160 | 0.141 |
| | 2[c] | 0.423 | 0.145 |
| 120 | 1[b] | 0.155 | 0.097 |
| | 2[c] | 0.478 | 0.189 |

[a]3
[b]Day 1 Predose Sample
[c]Post Dose Sample

Utility of the PEG-SOD formulations resides in the prevention and treatment of oxidative injury in a clinical setting.

Free oxygen radicals have been postulated as important mediators in a broad spectrum of clinical disorders, including life-threatening disease processes such as carcinogenesis and aging, and in ischemia-reperfusion injury. Studies have shown that free oxygen radicals ($O_2-.$) cause chemical modification of proteins, lipids, carbohydrates and nucleotides. Fluxes of $O_2-.$ have been shown to kill bacteria, inactivate viruses, lyse erthrocytes, destroy granulocytes, damage myoblasts in culture, depolymerize hyaluronate, modify low-density lipoprotein and damage DNA. Hydrogen peroxide may potentiate the effects of proteases (e.g., trypsin), resulting in a modification of protein substrates such as fibrinogen, hemoglobin and glomerular basement membrane, so that they become very susceptible to proteolysis. Other cytotoxic consequences of free radical formation and accumulation include alterations in membrane integrity and permeability, loss of enzyme activity due to denaturation of proteins and increased inflammatory response.

Endogenous scavenger enzymes such as superoxide dismutase (SOD) and catalase (CAT) normally remove toxic oxygen intermediates before they can cause tissue injury. However, during reperfusion, and in certain other clinical settings, the endogenous enzyme defense mechanisms may be overwhelmed. Supplementing these enzymes is of therapeutic benefit. Free radical scavengers such as SOD have been reported to attenuate ischemic-related damage accompanying reperfusion in several animal models. See, for example: Shlafer, M., Kane, P. F., Kirsch, M. M., "Superoxide Dismutase Plus Catalase Enhances the Efficacy of Hypothermic Cardioplegia to Protect the Globally Ischemic, Reperfused Heart", *J. Thorac Cardiovasc. Surg.*, 1982;83:630; Shlafer, M., Kane, P. F., Wiggins, V. Y., Kirsch, M. M., "Possible Role of Cytotoxic Oxygen Metabolites in the Pathogenesis of Cardiac Ischemic Injury", *Circ.* 1982;66(Suppl I):1–85; Casale, A. S., Bulkley, G. B., Bulkley, B. H., Flaherty, J. T., Gott, V. L., Gardner, T. J., "Oxygen Free-Radical Scavengers Protect the Arrested, Globally Ischemic Heart Upon Reperfusion", *Surg. Forum*, 1983;34:313; Stewart, J. R., Blackwell, W. H. A., Crute, S. L., Loughlin, V., Hess, M. L., Greenfield, L. J., "Prevention of Myocardial Ischemia/Reperfusion Injury with Oxygen Free Radical Scavengers", *Surg. Forum*, 1982;33:317; Pryzyklenk, K., Kloner, R. A., "Superoxide Dismutase Plus Catalase Improve Contractile Function in the Canine Model of the Stunned Myocardium", *Circ. Res.* 1986;58:148–156; and Beckman, J. S., Minor, R. L. Jr., White, C. W., Repine, J. E., Rosen, G. M., Freeman, B. A., "Superoxide Dismutase and Catalase Conjugated to Polyethylene Glycol Increases Endothelial Enzyme Activity and Oxidant Resistance", *J. Biol. Chem.* 1988;263(14):6884–6892.

In a method aspect, the present invention provides for preventing and/or treating oxidative injury in a mammal which treatment comprises administering to said mammal a therapeutically effective amount of a formulation of PEG-SOD in a pharmaceutically acceptable carrier. The amount of units of SOD to be administered parenterally will depend on the particular condition treated, the age, weight and other characteristics of the patient, which are to be judged by the physician. A dosage range of from about 2,000 to about 50,000 units per kg of body weight is envisaged for administration, while a range of from about 5,000 to about 25,000 units per kg of body weight is preferred.

While preferred embodiments of the invention have been described and illustrated in the specification, it is to be understood that such is merely illustrative of the underlying concept and features of the invention and are not to be limiting of the scope of the invention and the appended claims.

What is claimed is:

1. A biologically active proteinaceous composition comprising: polyethylene glycol having a molecular weight of from about 1,000 to about 15,000 daltons and consisting essentially of less than about 10% w/w non-monomethoxylated polyethylene glycol and at least about 90% w/w monomethoxylated polyethylene glycol covalently attached to superoxide dismutase; said proteinaceous composition having an immunoreactivity of less than 50% to mammalian antibodies than the immunoreactivity to mammalian antibodies of a proteinaceous composition comprising: polyethylene glycol having a molecular weight of from about 1,000 to about 15,000 daltons and consisting essentially of more than 10% w/w non-monomethoxylated polyethylene glycol and less than 90% w/w monomethoxylated polyethylene glycol covalently attached to superoxide dismutase.

2. The biologically active proteinaceous composition of claim 1 having an immunoreactivity to mammalian antibodies of from about 50% to about 1,000% less than the immunoreactivity to mammalian antibodies of a composition comprising: polyethylene glycol having a molecular weight of from about 1,000 to about 15,00 daltons and consisting essentially of more than 10% w/w non-monomethoxylated polyethylene glycol and less than 90% w/w monomethoxylated polyethylene glycol covalently attached to superoxide dismutase.

3. The biologically active proteinaceous composition of claim 1 wherein said superoxide dismutase is bovine superoxide dismutase.

4. The biologically active proteinaceous composition of claim 1 wherein said superoxide dismutase is recombinant superoxide dismutase.

5. The biologically active proteinaceous composition of claim 1 wherein said polyethylene glycol has a molecular weight of from about 2,000 to about 10,000 daltons.

6. The biologically active proteinaceous composition of claim 1 wherein said polyethylene glycol has a molecular weight of from about 4,000 to about 6,000 daltons.

7. The biologically active proteinaceous composition of claim 1 wherein said polyethylene glycol contains less than about 7% w/w non-methoxylated polyethylene glycol.

8. The biologically active proteinaceous composition of claim 1 wherein said polyethylene glycol contains less than about 5% w/w non-methoxylated polyethylene glycol.

* * * * *